United States Patent
Alpegiani, Jr. et al.

(10) Patent No.: US 9,163,034 B2
(45) Date of Patent: Oct. 20, 2015

(54) CRYSTALLINE (6R,7R)-7-{2-(5-AMINO-[1,2,4]THIADIAZOL-3-YL)-2-[(Z)-TRITYLOXYIMINO]-ACETYLAMINO}-3-[(R)-1'-TERT-BUTOXYCARBONYL-2-OXO-[1,3']BIPYRROLIDINYL-(3E)-YLIDENEMETHYL]-8-OXO-5-THIA-1-AZA-BICYCLO[4.2.0]OCT-2-ENE-2-CARBOXYLIC ACID BENZHYDRYL ESTER; ITS MANUFACTURE AND USE

(71) Applicant: Basilea Pharmaceutica AG, Basel (CH)

(72) Inventors: Marco Alpegiani, Jr., Milan (IT); Walter Cabri, Rozzano (IT); Markus Heubes, Schopfheim (DE); Davide Longoni, Gorgonzola (IT); Michael Schleimer, Inzlingen (DE)

(73) Assignee: BASILEA PHARMACEUTICA AG, Basel (CH)

( * ) Notice: Subject to any disclaimer, the term of this patent is extended or adjusted under 35 U.S.C. 154(b) by 0 days.

(21) Appl. No.: 14/486,205

(22) Filed: Sep. 15, 2014

(65) Prior Publication Data

US 2015/0005491 A1  Jan. 1, 2015

Related U.S. Application Data

(62) Division of application No. 12/937,607, filed as application No. PCT/EP2009/054405 on Apr. 14, 2009, now Pat. No. 8,865,697.

(30) Foreign Application Priority Data

Apr. 15, 2008 (EP) ..................................... 08154517

(51) Int. Cl.
*C07D 501/12* (2006.01)
*C07D 501/54* (2006.01)

(52) U.S. Cl.
CPC ............ *C07D 501/12* (2013.01); *C07D 501/54* (2013.01)

(58) Field of Classification Search
CPC .................................................... C07D 501/12
See application file for complete search history.

(56) References Cited

U.S. PATENT DOCUMENTS

| 4,237,279 | A | 12/1980 | Fisher |
| 4,734,408 | A | 3/1988 | Katner |
| 6,903,211 | B2 | 6/2005 | Deshpande et al. |

FOREIGN PATENT DOCUMENTS

| EP | 0849269 | 6/1998 |
| WO | 9965920 | 12/1999 |
| WO | 0190111 | 11/2001 |
| WO | WO 0190111 A1 * | 11/2001 |

OTHER PUBLICATIONS

The International Search Report and Written Opinion by the International Searching Authority, issued on Jun. 2, 2009, in the PCT application No. PCT/EP2009/054405.
The extended European Search Report, issued on Sep. 4, 2008, in the European application No. 08154517.0.

* cited by examiner

*Primary Examiner* — Andrew D Kosar
*Assistant Examiner* — John S Kenyon

(57) ABSTRACT

A solid DMSO solvate of a compound of formula (I) is described, which is a useful intermediate for preparing the broad spectrum antibiotics Ceftobiprole and Ceftobiprole Medocaril.

(I)

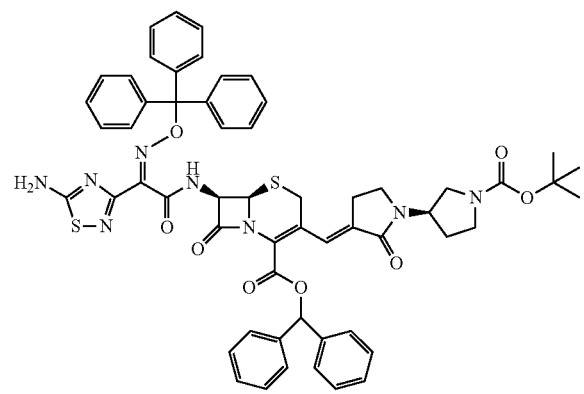

11 Claims, 3 Drawing Sheets

Molecule of the compound of formula (I) in three dimensions with a labeling scheme (see Example 2)

CRYSTALLINE (6R,7R)-7-{2-(5-AMINO-[1,2,4]THIADIAZOL-3-YL)-2-[(Z)-TRITYLOXYIMINO]-ACETYLAMINO}-3-[(R)-1'-TERT-BUTOXYCARBONYL-2-OXO-[1,3']BIPYRROLIDINYL-(3E)-YLIDENEMETHYL]-8-OXO-5-THIA-1-AZA-BICYCLO[4.2.0]OCT-2-ENE-2-CARBOXYLIC ACID BENZHYDRYL ESTER; ITS MANUFACTURE AND USE

This application is a divisional application of U.S. application Ser. No. 12/937,607, filed Feb. 18, 2011, which, in turn, is a National Stage Application of PCT/EP2009/054405 filed Apr. 14, 2009, which claims priority from European Patent Application 08154517.0, filed Apr. 15, 2008, the contents of all of which are expressly incorporated herein by reference. Priority of both said PCT and European Patent Applications is claimed.

The present invention relates to a solid, in particular a substantially crystalline DMSO solvate of the compound of formula (I) and to an improved process for the manufacture of the compound of formula (I):

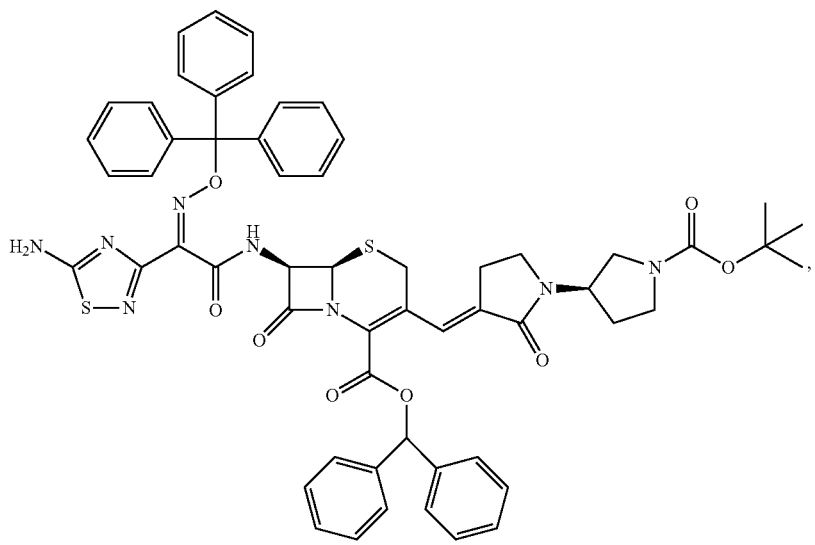

(I)

via said solvate. The compound of formula (I) is an intermediate for manufacturing certain cephalosporins, in particular the broad spectrum antibiotics Ceftobiprole (BAL9141-000) and Ceftobiprole Medocaril (BAL5788). The invention furthermore relates to processes for the manufacture of Ceftobiprole or Ceftobiprole Medocaril using said DMSO solvate and to a substantially crystalline form of the compound of formula (I).

The compound of formula I and its use in the manufacturing of the antibiotics Ceftobiprole (BAL9141-000) and Ceftobiprole Medocaril (BAL5788) are known.

As described in more detail in WO 01/90111, the compound (I) can e.g. be prepared by reacting (1'-tert-butoxycarbonyl-2-oxo-[1,3']-(R)-bipyrrolidinyl-3-(R,S)-yl)-triphenylphosphonium bromide with 7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester in a mixture of methylene chloride/toluene/THF in presence of t-C$_4$H$_9$OK. The raw wet compound of formula (I) obtained according to WO 01/90111 is conventionally purified, e.g. by slurrying it with methylene chloride and ethylacetate at ambient or slightly elevated temperature, and is then filtered off and dried. Following this procedure, the product precipitates in aggregates of rather small particles only, that determine poor filtration performance and therefore an insufficient impurities elimination. As a consequence, the intermediate obtained according to WO 01/90111 does not generate Ceftobiprole and Ceftobiprole Medocaril with acceptable purity and yield. The process is furthermore not very suitable for a large scale industrial manufacture.

For the manufacture of some cephalosporin derivatives it is known to convert the respective cephalosporin derivatives or an intermediate or precursor thereof into specific crystalline solvates, which are optionally further purified, and further processed to the desired cephalosporin compounds.

U.S. Pat. No. 4,734,408, for example, describes a manufacturing process for crystalline syn-7-[2-(2-aminothiazol-4-yl)-2-methoxyiminoacetamido]-3-(3-methyl-3-H-imidazolo[4,5-c]-pyridinium-5-ylmethyl)-3-cephem-4-carboxylate sulfate dihydrate wherein said cephalosporin derivative is e.g. dissolved in water to give an aqueous solution thereof, to which dimethylacetamide or dimethylformamide is added to form respective crystalline solvates, in particular a dimethylacetamide solvate hydrate or a dimethylformamide solvate hydrate of said cephalosporine derivative which is then re-dissolved in aqueous sulfuric acid. This solution may then be chilled and/or blended with a water-soluble anti-solvent for said cephalosporin derivative, like acetone, THF or acetonitrile, to effect the precipitation of the desired cephalosporine as a purified crystalline solid.

U.S. Pat. No. 4,237,279 describes a process for the purification and facile isolation of 4'-nitrobenzyl-7-phenoxyacetamido-3-hydroxy-3-cephem-4-carboxylate or its 1-oxide, which is an important intermediate in the manufacture of certain cephalosporins, in particular 7-[D-(2-amino-2-phenylacetamido)]3-chloro-3-cephem4-carboxylic acid. In this process said intermediate is converted into a crystalline solvate thereof selected from the acetic acid solvate, the propionic acid solvate or the methylene chloride solvate, which is then isolated and slurried with methanol to form a methanol solvate of said intermediate from which the methanol is then removed by drying the solvate under vacuum to give the anhydrous, unsolvated and purified 4'-nitrobenzyl-7-phenoxyacetamido-3-hydroxy-3-cephem-4-carboxylate or its 1-oxide.

U.S. Pat. No. 6,903,211 describes the manufacture of a further specific cephalosporin solvate, namely Cefprozil DMF-solvate, which is useful in the manufacture of Cefprozil. The process is described to avoid the use of adsorption chromatography or re-crystallization methods at any stage, to be thus easy to operate on an industrial scale and to result in an enrichment of the desired (Z)-isomer of the solvate.

Notwithstanding the use of certain crystalline solvates in all the aforementioned processes, it is clearly visible that said manufacturing processes are specifically tailored just to the manufacture of those cephalosporins to which each of the respective references specifically refer. There is no indication, neither in said references nor in the prior art in general, that the processes and/or solvate-types disclosed in said references could, in an analogous manner, successfully be used in the manufacture of other cephalosporins, too. There is neither any indication in the prior art, that the common strategy disclosed in these references, namely to use the intermediate manufacture of a certain solvate as a means for improving the purity of final products could be used for other cephalosporin derivatives at all. And last but not least, there is not any guidance at all in said references, which solvate could successfully be used for other cephalosporin derivatives and particularly in the manufacture of Ceftobiprole or Ceftobiprole Medocaril.

Thus it is still an unsolved problem to overcome the above-mentioned disadvantages of the prior art concerning the manufacture of the afore-mentioned cephalosporin derivatives via the compound of formula (I) as intermediate. Accordingly, it is an objective of the present invention to provide improvements concerning the performance of the manufacture Ceftobiprole or Ceftobiprole Medocaril, in particular on an industrial scale, and to improve the purity of said cephalosporins at the same time.

The present invention is based on the new finding that the purification of the compound of formula (I) can also significantly be improved if a specific solvate of said compound, namely a DMSO (dimethylsulfoxide) solvate of said compound, is used as an intermediate in the manufacture, which is isolated, and the isolated solvate is then re-converted, optionally in wet condition, into the compound of formula (I) which is generally obtained in substantially crystalline form in this way. It has furthermore been found that the final cephalosporin derivatives, Ceftobiprole or Ceftobiprole Medocaril, if manufactured according to the present invention via said DMSO solvate of the compound of formula (I) are also significantly improved in purity as compared to the prior art manufacture.

Accordingly, the present invention concerns a solid DMSO solvate of the compound of formula (I), a substantially crystalline embodiment of said DMSO solvate, a process for the manufacture of said solvate, an improved process for the manufacture of a compound of formula (I) via said solvate, a substantially crystalline form of the compound of formula (I) which is obtainable with said process and which is a valuable intermediate in particular for the manufacture of high purity Ceftobiprole and Ceftobiprole Medocaril and an improved processes for the manufacture of Ceftobiprole and Ceftobiprole Medocaril via the new intermediates according to the present invention.

Accordingly, a first subject of the present invention is a solid DMSO solvate of the compound of formula (I)

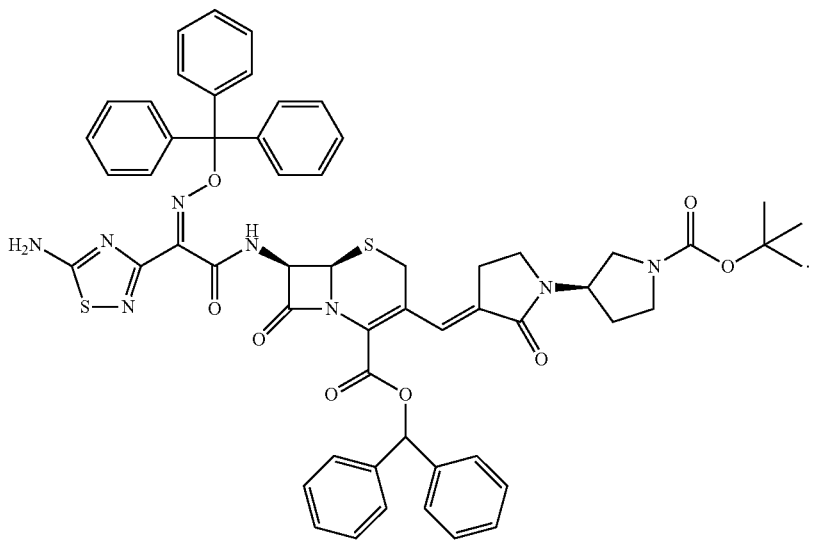 [SMILES: CC(C)(C)OC(=O)N1CC[C@@H](N2CC/C(=C\C3=C(C(=O)OC(c4ccccc4)c4ccccc4)N4C(=O)[C@@H](NC(=O)/C(=N\OC(c5ccccc5)(c5ccccc5)c5ccccc5)c5nsc(N)n5)[C@H]4SC3)C2=O)C1]

The molar ratio of the compound of formula (I) and DMSO in said solid DMSO solvate is generally from about 1:1 to 1:3, in particular from about 1:1.75 to about 1:2.75. Most preferred is molar ratio of the compound of formula (I) and DMSO from about 1:2 to about 1:2.5, and the term "DMSO solvate according to the invention" in the present application is meant to refer preferably to the DMSO solvate having a molar ratio from about 1:2 to about 1:2.5, if nothing else is stated. With regard to molar ratio of the compound of formula (I) and DMSO the term "about" is used to include minor variations, generally of ±10 percent maximum, to allow for certain amounts of free DMSO possibly adhering to or incorporated into the material and for other usual variations of measurement.

For the purposes of this application the term "solid" is understood in the usual way, namely that the substance indicated as being "solid" has a melting temperature or, if the substance decomposes before it melts, a decomposition temperature, which is above usual ambient temperatures, in particular above about 25 to 30° C.

For the purposes of this application the term "substantially crystalline" means that a X-Ray Powder Diffraction (XRPD) diagram of a corresponding substance shows one or more distinct peaks which have a maximum height corresponding to at least the fivefold, preferably the sevenfold of their width at half-maximum. Generally, the degree of crystallinity of a substance increases with an increasing average value for the ratio of the height of a certain peak to its width at half-maximum. X-ray reflections at a rather low angel 2Theta and/or of major relative intensity are normally more meaningful for evaluating the degree of crystallinity of a compound because at higher angels 2Theta there is often an overlap of several reflections which then appear as one broad peak, in particular if said reflections are of rather low intensity. In addition to exhibiting a plurality of sharp peaks, the XRPD diagram shall furthermore show a substantially constant baseline (baseline=a line connecting the minima of the XRPD diagram curve) over the entire scanned 2Theta range, indicating the substantial absence of amorphous material in the recorded sample. "Substantially constant base line" means for the purposes of this application that the baseline does preferably not rise for more than the height of the lowest peak of said diagram.

A substantially crystalline or crystalline DMSO solvate according to the present invention exhibits X-Ray Powder Diffraction peaks as defined in the preceding paragraph and recorded with Cu K-alpha Radiation) and given in [° 2Theta] at about 7.0; 13.7; 18.0; 19.0; 19.9; 20.1; 20.2; 22.1; 22.8; 23.0; 23.3, all of which have a relative Intensity of more than about 55%.

An average sample of the DMSO solvate of a compound of formula (I) as described above exhibits essentially the X-Ray Powder Diffraction pattern listed in Table 1 below, although there may be slight deviations in the exact values for 2Theta and particularly the relative Intensity (Rel. Int.) between different charges of the solvate and depending on the preparation of the XRPD test sample, as those skilled in the art will appreciate. The 2Theta angles have generally an error of about ±0.2°. It is known, however, that the values for the relative Intensity of the peaks are more dependent from certain properties of the measured sample than the line position, e.g. from the size of the crystals and their orientation in the sample. Variations of ±20% of the shown peak intensities are therefore likely to occur.

It should also be noted that Table 1 lists only the peaks with a relative Intensity of about 30% minimum, the presence of which is normally sufficient for characterizing the crystals, and it is clear therefore that further peaks may still be found in the XRPD pattern of said solvate.

TABLE 1

| 2Θ [°] | Rel Int* |
|---|---|
| 6.7 | w |
| 7.0 | m |
| 13.7 | m |
| 17.5 | w |
| 18.0 | vst |
| 18.5 | w |
| 19.0 | vst |
| 19.3 | w |
| 19.9 | vst |
| 20.1 | m |
| 20.2 | st |
| 20.6 | w |
| 21.1 | w |
| 22.1 | m |
| 22.8 | m |

TABLE 1-continued

| 2Θ [°] | Rel Int* |
|---|---|
| 23.0 | m |
| 23.3 | m |
| 26.8 | w |
| 27.3 | m |
| 32.2 | w |

*In Table 1 vst stands for a relative intensity of 100% to 90%; st stands for a relative intensity of less than 90% to 75%; m stands for a relative intensity of less than 75% to 55%; and w stands for a relative intensity of less than 55% to 30%.

Table 2 shows the numerical values for the relative intensities of the 20 major intensive XRPD peaks of a typical sample of the DMSO solvate according to the invention and gives an indication of the typical variations of the measured values for the relative Intensity.

TABLE 2

| 2Θ [°] | Rel Int [%] |
|---|---|
| 6.7 | 35 ± 7 |
| 7.0 | 65 ± 13 |
| 13.7 | 58 ± 12 |
| 17.5 | 46 ± 9 |
| 18.0 | 100 ± 20 |
| 18.5 | 47 ± 9 |
| 19.0 | 93 ± 19 |
| 19.3 | 47 ± 9 |
| 19.9 | 87 ± 18 |
| 20.1 | 68 ± 14 |
| 20.2 | 77 ± 15 |
| 20.6 | 50 ± 10 |
| 21.1 | 39 ± 8 |
| 22.1 | 64 ± 13 |
| 22.8 | 62 ± 12 |
| 23.0 | 68 ± 14 |
| 23.3 | 69 ± 14 |
| 26.8 | 44 ± 9 |
| 27.3 | 54 ± 11 |
| 32.2 | 31 ± 6 |

A further subject of the present invention is a preferred process for the manufacture of a substantially crystalline or crystalline DMSO solvate of the compound of formula (I) as described above, wherein a raw compound of formula (I) is suspended in ethyl acetate, DMSO is added to said suspension in an amount being sufficient to dissolve all or at least substantially all of the compound of formula (I) and wherein the DMSO solvate of the compound of formula (I), which crystallizes from the solution, is separated from the liquid phase.

In another aspect the present invention relates to a preferred process for the manufacture of a purified form of the compound of formula (I) from a raw form of said compound, wherein the raw compound of formula (I) is converted into a solid DMSO solvate as described above, preferably into a corresponding substantially crystalline or crystalline DMSO solvate, in particular in the way described in this application, and more particularly into a substantially crystalline or crystalline DMSO solvate, wherein the molar ratio of the compound of formula (I) and DMSO is from about 1:1:75 to 1:2.75, which DMSO solvate is isolated, preferably in wet form, and re-dissolved in methylene chloride, in which the compound of formula (I) precipitates, and said precipitated purified compound of formula (I) is isolated.

The invention also relates to the compound of formula (I) as obtainable by the process described in the preceding paragraph.

The invention furthermore relates to a compound of formula (I) which essentially exhibits the following X-Ray Powder Diffraction pattern recorded with Cu K-alpha radiation by which it can be easily characterized:

| 2Θ [°] | Rel Int [%] |
|---|---|
| 4.7 | 100 ± 20 |
| 6.2 | 21 ± 4 |
| 9.1 | 9.5 ± 2 |
| 9.3 | 15.5 ± 3 |
| 9.6 | 11.5 ± 2 |
| 11.8 | 12 ± 2 |
| 14.5 | 10 ± 2 |
| 15.8 | 10 ± 2 |
| 16.1 | 18 ± 4 |
| 18.3 | 14 ± 3 |
| 18.4 | 13.5 ± 3 |
| 18.7 | 10.5 ± 2 |
| 20.6 | 14.5 ± 3 |
| 21.8 | 9.5 ± 2 |
| 22.3 | 13.5 ± 3 |
| 22.7 | 13 ± 3 |
| 23.9 | 10.5 ± 2 |
| 25.2 | 11 ± 2 |
| 28.1 | 9 ± 2 |

The measurement error of the 2Theta values is generally ±0.2°, typical variations of the indicated values for the relative intensity are given in the table.

Still another subject of the present invention is a compound of the afore-mentioned formula (I) comprising crystals having the following crystal parameters:

| | | |
|---|---|---|
| Crystal system | Monoclinic | |
| Space group | C2 | |
| Unit cell dimensions | a = 39.292(6) Ang | alpha = 90°. |
| | b = 9.955(2) Ang | beta = 103.191(10)°. |
| | c = 16.813(2) Ang | gamma = 90°. |
| Volume | 6402.8(18) (Ang)$^3$ | |
| Z | 4 formula units per unit cell | |
| Density (calculated) | 1.167 Mg/m$^3$. | |

Figure 1:
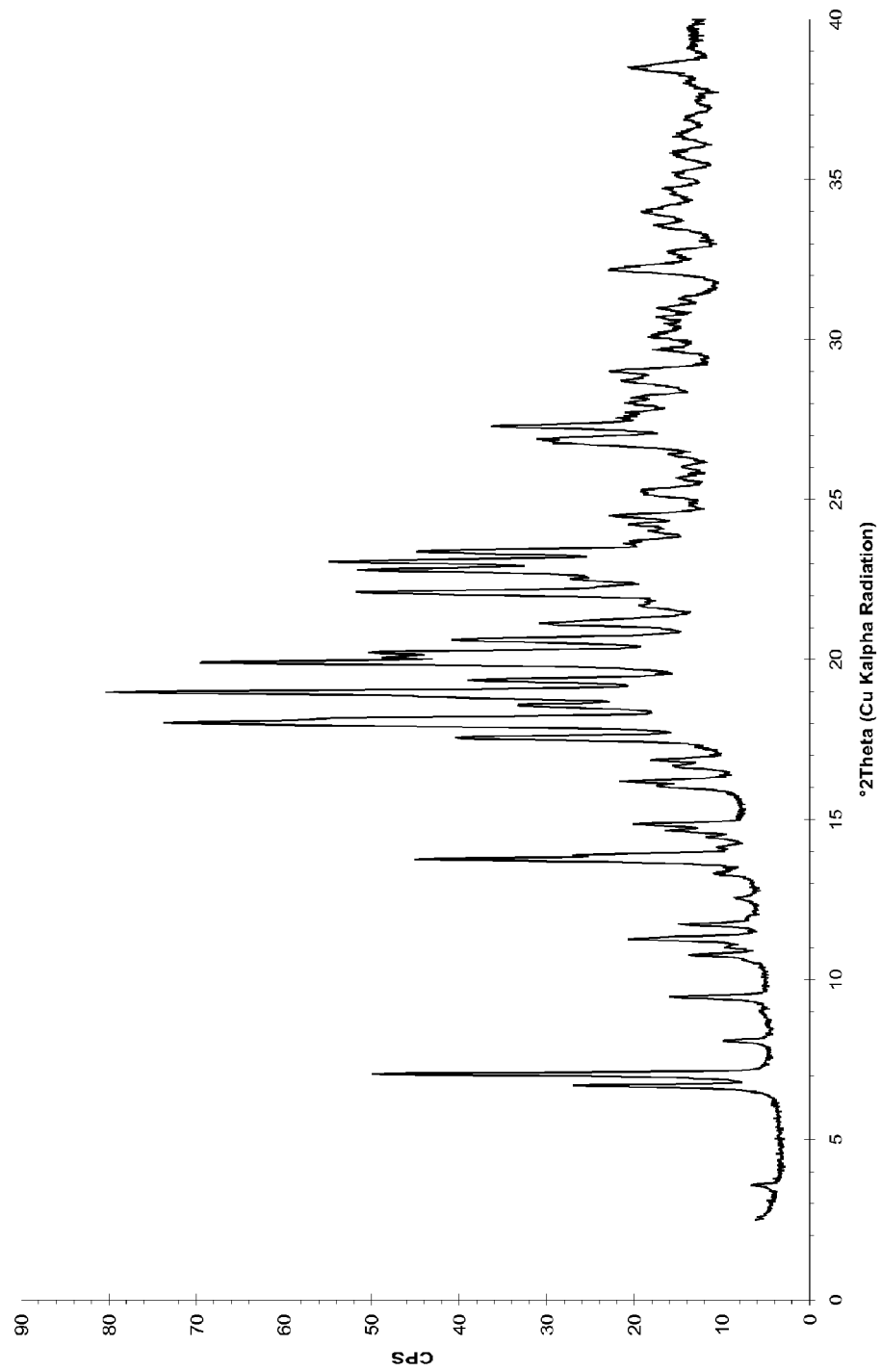
FIG. 1 shows a typical XRPD diagram of a DMSO solvate of the compound of formula (I) according to the invention.
Figure 2:
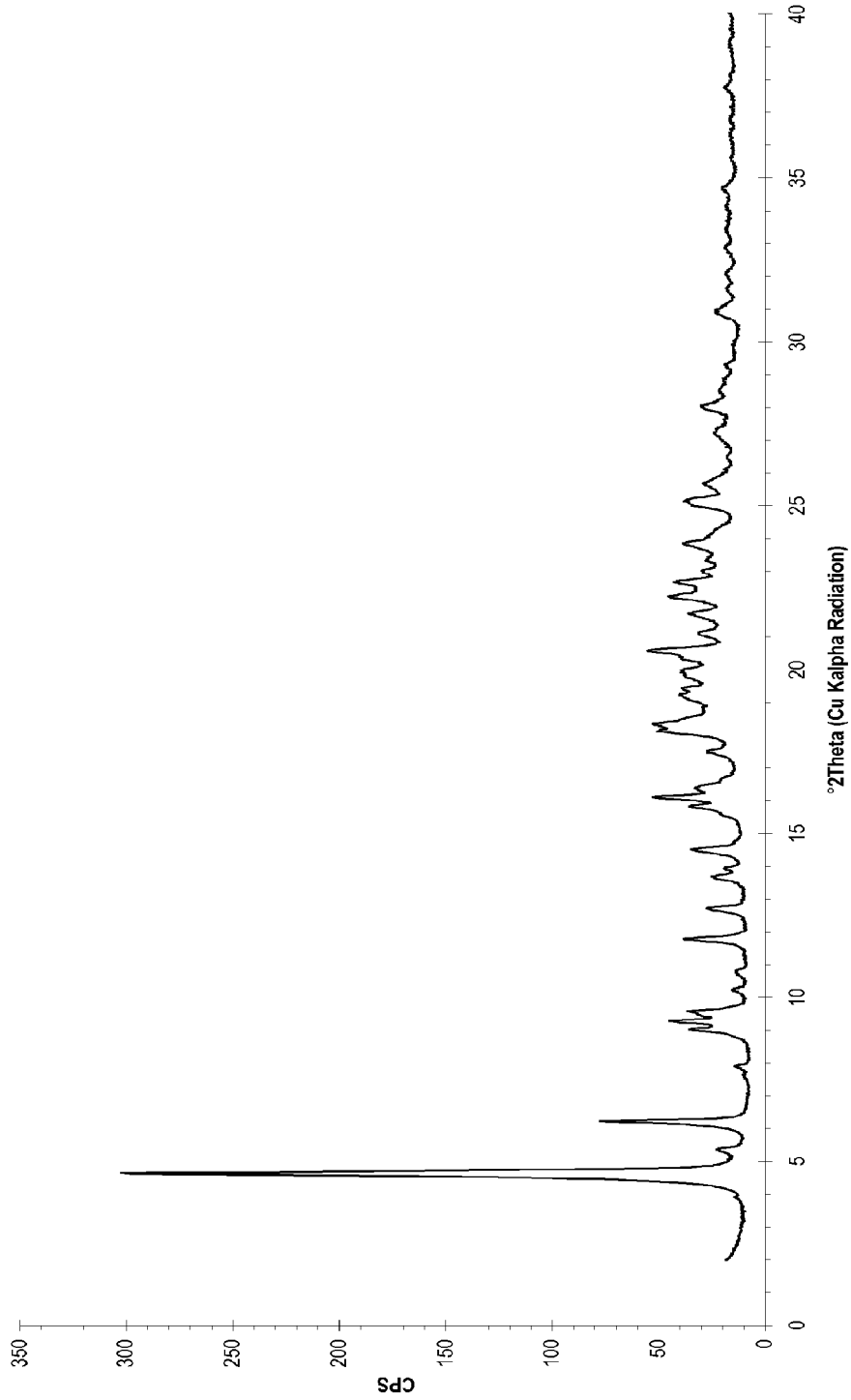
FIG. 2 shows a typical XRPD diagram of the compound of formula (I) as obtainable via its DMSO solvate according to the invention.

In yet another aspect the present invention relates to a process for the manufacture of Ceftobiprole, i.e. the compound of formula II:

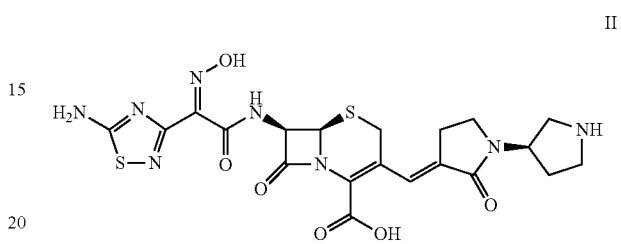

II wherein a compound of formula (I) is converted into a solid DMSO solvate, in particular in the way described herein and more particularly into a substantially crystalline or crystalline DMSO solvate, wherein the molar ratio of the compound of formula (I) and DMSO is from about 1:1.75 to 1:2.75, preferably from about 1:2 to about 1:2.5, which solid DMSO solvate is isolated, preferably in wet form, and re-dissolved in methylene chloride, in which the compound of formula (I) precipitates, and the purified precipitated compound of formula (I) is isolated and converted to Ceftobiprole. The conversion to Ceftobiprole can be performed as described e.g. in EP 0 849 269 or WO 99/65920 or in an analogous way, e.g. by removing the protecting groups through treatment with trifluoroacetic acid and triethylsilane followed by neutralization with sodium hydrogen carbonate.

The invention furthermore relates to a process for the manufacture of Ceftobiprole Medocaril, i.e. the compound of formula III:

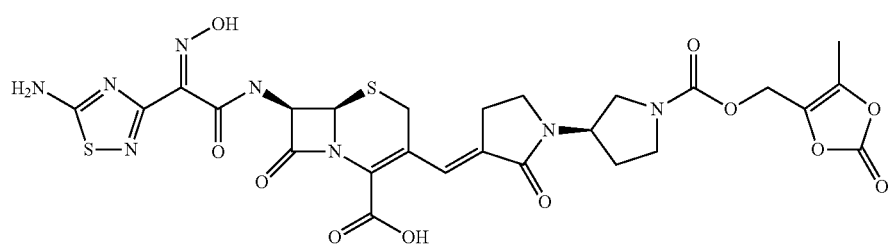

III or Ceftobiprole Medocaril in form of its sodium salt, i.e. the compound of formula:

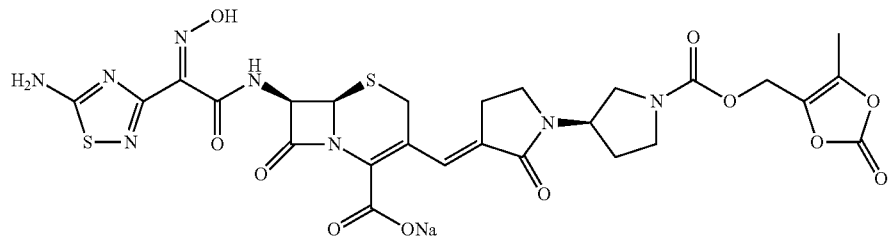

wherein a compound of formula (I) is converted into a solid DMSO solvate, in particular in the way described herein and more particularly into a substantially crystalline or crystalline DMSO solvate, wherein the molar ratio of the compound of formula (I) and DMSO is from about 1:1.75 to 1:2.75, preferably from about 1:2 to about 1:2.5, which solid DMSO solvate is isolated, preferably in wet form, and re-dissolved in methylene chloride, in which the compound of formula (I) precipitates, and the purified precipitated compound of formula (I) is isolated and converted to Ceftobiprole Medocaril (formula III) and its sodium salt. The latter conversion can e.g. be performed as described in WO01/90111, e.g. by treatment with carbonic acid 5-methyl-2-oxo-[1,3]dioxol-4-ylmethyl ester 4-nitro-phenyl ester in DMSO and optionally subsequent precipitation of the sodium salt thereof by treatment with sodium ethylhexanoate.

More particularly, it has been found that the DMSO solvate according to the present invention precipitates from a mixture of ethyl acetate and DMSO at ambient temperatures, generally from about 15° C. to 30° C., e.g. 20 to 27° C. like, for instance, about 25° C., whereas the pure compound of formula (I) is readily soluble is such mixtures at said temperatures. It is therefore possible to dissolve the raw compound of formula (I) in a mixture of ethyl acetate and DMSO. The less soluble DMSO solvate according to the present invention precipitates from said solvent mixture. This DMSO solvate generally contains less impurities than the raw compound of formula (I). Furthermore, the DMSO solvate forms crystals under said conditions which are relatively large in size, so that they can readily and very fast be separated from the solvent, e.g. by centrifugation and/or filtration.

In methylene chloride, on the other hand, the DMSO solvate according to the present invention is readily soluble at temperatures in the range as indicated in the preceding paragraph (solubility about 70 g/l at about 25° C.). The compound of formula (I) is significantly less soluble in methylene chloride under said conditions (solubility about 8 g/l at about 25° C.). Therefore dissolving the DMSO solvate methylene chloride results in that the compound of formula (I) precipitates from this solution. This precipitate of the compound of formula (I) is generally again of greater purity than the DMSO solvate dissolved, and of such a particle size, that it can very fast be filtered or centrifuged off from the solvent. Furthermore, the precipitate of compound of formula (I) is generally in substantially crystalline form when precipitated from methylene chloride. More particularly, the precipitate comprises the compound of formula (I) at least partially in form of single-crystals.

Both aforementioned crystallization steps strongly increase the purity of the raw compound of formula (I). The percentage of compound of formula (I) in the material generally increases from about 84 to 87 percent in the raw material to about 97 and more percent in the purified material, which has been recovered from the DMSO solvate according to the present invention. The following Table shows the purification effect of the process according to the present invention for three industrial batches of the compound of formula (I).

TABLE 3

Comparison between the purity of raw compound of formula I ["BAL1026 raw"], the DMSO solvate obtained therefrom ["BAL1026 solvate"] and the recovered purified compound of formula I ["BAL1026 recovered"]. The percentage indicates the quantity of the desired product in the total material obtained and is determined with LC (liquid chromatography).

| Product | Batch No. | Purity (area %) |
|---|---|---|
| BAL1026 raw | 05R0004 | 84.4 |
| BAL1026 solvate | 05R0004 | 95.2 |

TABLE 3-continued

Comparison between the purity of raw compound of formula I ["BAL1026 raw"], the DMSO solvate obtained therefrom ["BAL1026 solvate"] and the recovered purified compound of formula I ["BAL1026 recovered"]. The percentage indicates the quantity of the desired product in the total material obtained and is determined with LC (liquid chromatography).

| Product | Batch No. | Purity (area %) |
|---|---|---|
| BAL1026 recovered | 05R0004 | 97.0 |
| BAL1026 raw | 06R0001 | 87.4 |
| BAL1026 solvate | 06R0001 | 95.8 |
| BAL1026 recovered | 06R0001 | 97.3 |
| BAL1026 raw | 06R0002 | 86.0 |
| BAL1026 solvate | 06R0002 | 94.3 |
| BAL1026 recovered | 06R0002 | 97.0 |
| BAL1026 raw | 06R0014 | 86.3 |
| BAL1026 solvate | 06R0014 | 95.4 |
| BAL1026 recovered | 06R0014 | 97.3 |

Furthermore, the purity of the compound of formula (I), when purified via a solid DMSO solvate as intermediate according to the present invention, is much better than the purity of a corresponding conventionally purified material. This is evident from Table 4. The purity of the compound of formula (I) accordingly is about 90 percent for a conventionally manufactured batch and about 97 percent in batches manufactured according to the present invention.

TABLE 4

| | Production Batches of Compound (I) | | | | | |
|---|---|---|---|---|---|---|
| | Prior Art | | | Present Invention | | |
| | 03/001 Area % | 03/002 Area % | 03/003 Area % | 04R0001 Area % | 04R0002 Area % | 04R0003 Area % |
| Compound (I) | 90.6 | 89.9 | 90.7 | 96.8 | 97.3 | 97.1 |

As already mentioned above, it has also been found, that the process for the manufacture of the compound of formula (I) according to the present invention advantageously leads to material comprising the compound of formula (I) at least partially in form of single-crystals. Such single crystals have the above mentioned single crystal parameters and have, according to the inventors' best knowledge, not yet been made available to the public before.

When carrying out the preferred purification process for the compound of formula (I) according to the present invention, raw compound of formula (I) is suspended in ethyl acetate to form a slurry.

The process for manufacturing the raw compound of formula (I) is not critical for the present invention. In particular, it has been found, that the purification of said compound via its DMSO solvate according to the present invention results in material of equable quality, such as crystallinity and, in particular, purity, independently of the purity of the previous process intermediates for the material of formula (I).

The raw compound of formula (I) is optionally dried before purification.

Preferably, the ratio of raw compound of formula (I) and ethyl acetate is from 1 to 10 to 1 to 40 (weight/volume) in said slurry. While a lower amount of ethyl acetate as corresponding to a ratio of 1:10 results in a difficult agitation of the slurry, amounts of ethyl acetate corresponding to a ratio of 1:40 and more result in slower filtration of the DMSO solvate. More preferably, the ratio of raw solid compound of formula (I) and ethyl acetate is therefore from 1 to 15 to 1 to 20 (weight/volume), in particular about 1 to 17 (weight/volume).

After slurrying the compound of formula (I) in the ethyl acetate, DMSO is added to said suspension in an amount to dissolve all or at least substantially all of the compound of formula (I). The preferred ratio of formula I to DMSO ranges from 1 to 20 to 1 to 26, Most preferred is a ratio of about 1 to 23.

During the formation of the solvate the temperature of the reaction mixture may be held at about 15 to 50° C. Surprisingly however, it has turned out that it is possible to use ambient temperatures during solvate formation without any detrimental effect on the quality of the product. It is therefore preferred to held the temperature at about 20 to 30° C., in particular at about 23 to 27° C., during the formation of the solvate.

The formation of the solvate of the compound of formula (I) is usually finished within a time period of about 15 minutes to several hours, e.g. within 1 to 10, preferably 2 to 6 hours.

After the time period for solvate formation and/or crystal growth thereof, the suspension of precipitated and/or precipitating DMSO solvate is advantageously cooled to a temperature of about minus 5 to 10° C., preferably 0 to 4° C., and held at that temperature, optionally with stirring, for some further time, e.g. for about 0.25 to 5 hours, preferably 1 to 3 hours, before separating the DMSO solvate from the mother liquor.

Separation of the precipitated DMSO solvate can advantageously be accomplished by centrifugation and/or filtration because filtration times are very short due to the excellent crystallinity of the DMSO solvate according to the invention.

The isolated DMSO solvate of the compound of formula (I) can be further processed as it is, in order to recover the compound of formula (I), or can optionally also be previously dried.

The compound of formula (I) which can be recovered from said solvate according to the present invention is, in general, of significantly improved purity when compared to the purity of the solvate and particularly when compared to the raw compound of formula (I).

For recovering the compound of formula (I), the isolated solid DMSO solvate of the compound of formula (I), in particular a DMSO solvate manufactured as described above and more particularly a DMSO solvate, wherein the molar ratio of the compound of formula (I) and DMSO is about 1:2 is re-dissolved in such a quantity of methylene chloride. The purified compound of formula (I) precipitates in said solvent and is then isolated.

The isolated DMSO solvate is preferably added to the solvent at ambient or slightly elevated temperatures, e.g. in the range of 20 to 30° C., more preferably 23 to 27° C. The obtained mixture is then advantageously allowed to stand for some time, e.g. for about 15 minutes to a few hours, preferably for about 1 to 2 hours, and preferably with stirring, to allow proper crystallization of the compound of formula (I).

Then the reaction mixture is advantageously cooled, e.g. to a temperature of about 0 to 4° C., and allowed to further stand at said temperature for some time, e.g. for 30 minutes to 5 hours, preferably for 1 to 3 hours, before separating the precipitate of compound of formula (I) formed during said process step.

The precipitate is then centrifuged of filtered, optionally washed, and dried under vacuum to obtain the purified compound of formula (I).

The purified compound of formula (I) is preferably further processed to produce Ceftobiprole by cleaving off the trityl, the benzhydryl and the tert-butoxycarbonyl protective groups. Methods therefore are commonly known to those skilled in the art and e.g. described in more detail in WO 01/90111 or EP-A 0 849 269.

In an also preferred alternative, the purified compound of formula (I) is further processed to produce Ceftobipole Medocaril. This may e.g. be done according to the WO 01/90111 by converting the purified compound of formula (I) to Ceftobiprole as described above and reacting it with carbonic acid 5-methyl-2-oxo-[1,3]dioxol-4-ylmethyl ester 4-nitro-phenyl ester.

Using the purified compound of formula (I) as obtained according to the present invention for the manufacture of Ceftobiprole or Ceftobiprole Medocaril results in a significantly improved quality of said final cephalosporin products, Ceftobiprole or Ceftobiprole Medocaril, the purity (amount of the desired compound in the manufactured end product) of which is generally increased by about 2 to 3 percent (absolute). Furthermore and, the yield of the end products are significantly improved, too, because further purification steps necessary in the conventional prior art processing of said compounds can be avoided when working according to the present invention.

EXAMPLE 1

This example shows the purification of an industrial batch of the compound of formula (I) manufactured according to the following Synthesis Scheme ("Compound (I)"):

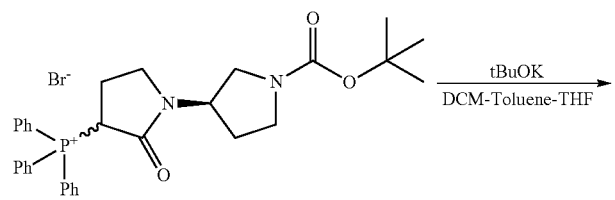

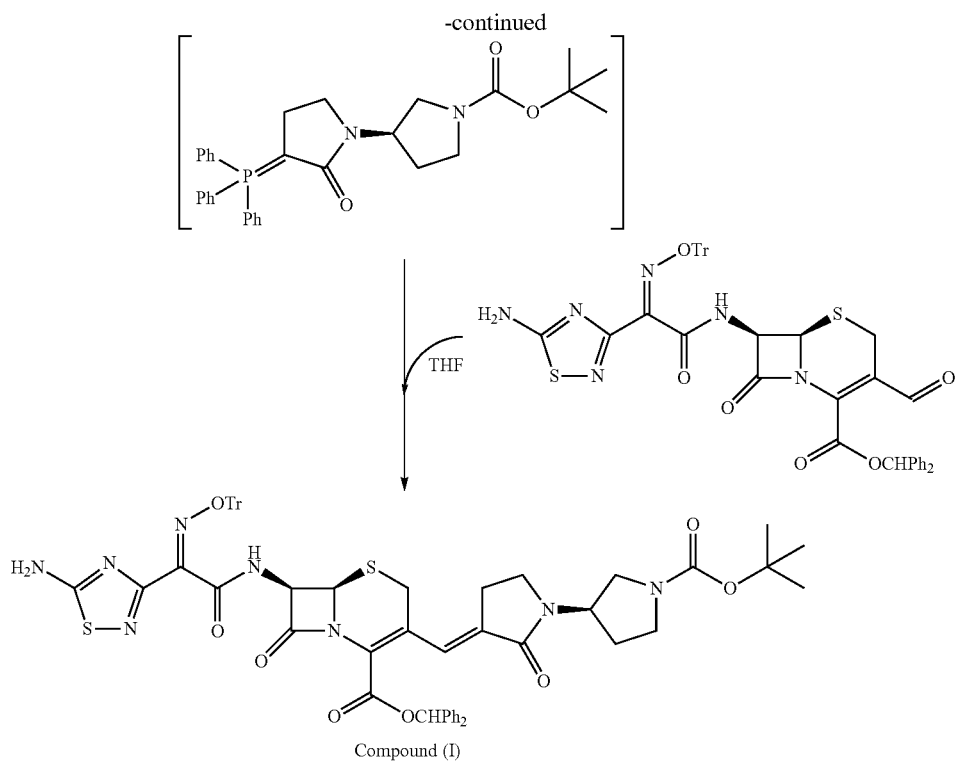

Compound (I)

Description of the Method

The reactor is charged with approx. 1 mol of wet raw compound (I) and 10.4 l of ethyl acetate. The mixture is warmed up to 23-27° C. and stirred. After 15 min additional 10.4 l of ethyl acetate are added and the solvent volume is reduced through vacuum distillation before 1.84 kg of DMSO are added dropwise within 15 min. The mixture is stirred until almost all material is dissolved.

The compound (I) crystallizes as DMSO solvate from the reaction mixture. Then additional 6.9 l of ethyl acetate are added and the resulting suspension is stirred for 0.25 h at 0-5° C. The solid DMSO solvate of Compound (I) is isolated by centrifugation and washed in the centrifuge with additional 1.85 l of ethyl acetate.

The wet DMSO solvate of Compound (I) (approx. 3 kg) is then dissolved at 23-27 C with 13.8 l methylene chloride (DCM). From this solution crystallizes the purified Compound (I). Further 13.8 l of ethyl acetate are added. The resulting suspension is stirred for 0.5 h at 0-5° C. and centrifuged. The purified product is washed with methylene chloride/ethyl acetate 1/1 (v/v) and dried in vacuo.

EXAMPLE 2

Determination of the absolute configuration of (6R, 7R)-7-{2-(5-Amino-[1,2,4]thiadiazol-3-yl)-2-[(Z)-trityloxyimino]-acetylamino}-3-[(R)-1'-tert-butoxycarbonyl-2-oxo-[1,3']bypyrrolodinyl-(3E)-ylidenemethyl]-8-oxo-5-thia-1-aza-bicyclo[4.2.0]oct-2-ene-2-carboxylic acid benzhydryl ester (Compound of formula (I)) by Single Crystal X-Ray Structure Analysis Measured Crystal: Colorless plate 0.050×0.040×0.006 mm$^3$
Chirality: R(C24); R(C29); R(C49);
Experimental For obtaining a single crystal suitable for X-Ray-Single Crystal Analysis about 20 mg of the above mentioned DMSO solvate of the compound of formula (I) were dissolved into an sufficient amount of acetonitrile to obtain a clear solution. This solution was allowed to evaporate very slowly at room temperature. An appropriate single crystal was then chosen out of the crystalline precipitate under the microscope. Crystal structure determination was carried out using a Bruker-Nonius diffractometer equipped with a Proteum-CCD area detector, a FR591 rotating anode with $CuK_0$ radiation, Montel mirrors as monochromator and a Kryoflex low temperature device (T=90 K). Fullsphere data collection omega and phi scans. Programs used: Data collection Proteum V. 1.37 (Bruker-Nonius 2002), data reduction Saint+Version 6.22 (Bruker-Nonius 2001) and absorption correction SADABS V. 2.03 (2002). Crystal structure solution was achieved using direct methods as implemented in SHELXTL Version 6.10 (Sheldrick, Universtitat Gottingen (Germany), 2000) and visualized using XP program. Missing atoms were subsequently located from difference Fourier synthesis and added to the atom list. Least-squares refinement on F2 using all measured intensities was carried out using the program SHELXTL Version 6.10 (Sheldrick, Universtitat Gbttingen (Germany), 2000). All non hydrogen atoms were refined including anisotropic displacement parameters.

Chirality

| Chirality Check* | Correct structure | Inverted structure |
| --- | --- | --- |
| Flack Parameter (standard deviation) | 0.024 (0.030) | 0.955 (0.032) |
| Twin Basf (standard deviation) | 0.02 (0.03) | 0.98 (0.03) |
| wR2-value (with Flack Parameter) | 0.2322 | 0.2485 |
| Chirality | R(C24); R(C29); R(C49) | S(C24); S(C29); S(C49) |

*H. D. Flack, *Acta Cryst*, 1983, A39, 876-881 H. D. Flack, G. Bernardinelli, *Acta Cryst*, 1999, A55, 908-915 H. D. Flack, G. Bernardinelli, *J. Appl. Cryst*, 2000, 33, 1143-1148.

Tables

TABLE 1

Crystal data and structure refinement.

| | |
|---|---|
| Empirical formula | C59.45 H54 N8.98 O10.42 S2 |
| Formula weight | 1125.07 |
| Temperature | 90(2) K |
| Wavelength | 1.54178 Angstroem (Ang) |
| Crystal system | Monoclinic |
| Space group | C2 |
| Unit cell dimensions | a = 39.292(6) Ang   alfa = 90°. |
| | b = 9.955(2) Ang   beta = 103.191(10)°. |
| | c = 16.813(2) Ang   gamma = 90°. |
| Volume | 6402.8(18) Ang$^3$ |
| Z | 4 |
| Density (calculated) | 1.167 Mg/m$^3$ |
| Absorption coefficient | 1.252 mm$^{-1}$ |
| F(000) | 2356 |
| Crystal size | 0.050 × 0.040 × 0.006 mm$^3$ |
| Theta range for data collection | 2.70 to 71.32° |
| Index ranges | −47 ≤ h ≤ 43, −12 ≤ k ≤ 10, −20 ≤ 1 ≤ 20 |
| Reflections collected | 28170 |
| Independent reflections | 10433 [R(int) = 0.0622] |
| Completeness to theta = 71.32° | 92.6% |
| Absorption correction | SADABS (Bruker-AXS) |
| Refinement method | Full-matrix least-squares on F$^2$ |
| Data/restraints/parameters | 10433/1/804 |
| Goodness-of-fit on F$^2$ | 0.999 |
| Final R indices [I > 2sigma(I)] | R1 = 0.0777, wR2 = 0.2128 |
| R indices (all data) | R1 = 0.1068, wR2 = 0.2322 |
| Absolute structure parameter | 0.02(3) |
| Largest diff. peak and hole | 0.421 and −0.329 e.(Ang)$^{-3}$ |

TABLE 2

Figure 3:
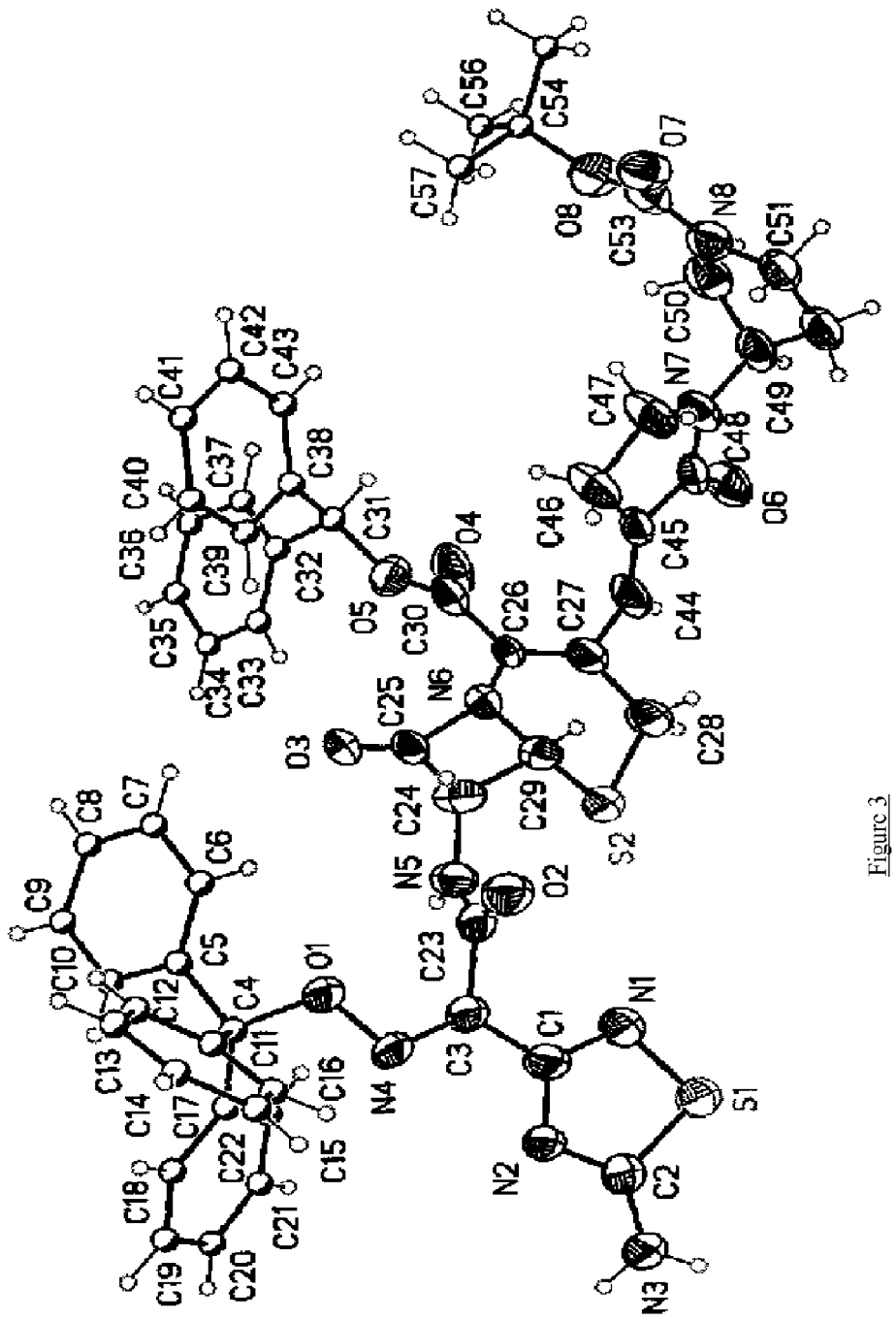
FIG. 3 depicts the molecule of the compound of formula (I) in three dimensions with a labeling scheme as calculated from X-ray analysis.

Bond lengths [Ang] and angles [°] (cf. FIG. 3)

| | | | | | |
|---|---|---|---|---|---|
| S(1)—N(1) | 1.690(5) | C(12)—C(13) | 1.405(10) | C(54)—C(55) | 1.501(12) |
| S(1)—C(2) | 1.749(6) | C(13)—C(14) | 1.388(10) | C(54)—C(56) | 1.530(11) |
| N(1)—C(1) | 1.324(7) | C(14)—C(15) | 1.398(11) | C(54)—C(57) | 1.536(12) |
| O(1)—N(4) | 1.408(5) | C(15)—C(16) | 1.385(9) | N(1L)—N(3L) | 0.82(2) |
| O(1)—C(4) | 1.490(6) | C(17)—C(22) | 1.378(9) | N(1L)—N(2L) | 0.97(4) |
| C(1)—N(2) | 1.351(6) | C(17)—C(18) | 1.405(8) | N(1L)—C(2LB) | 1.11(3) |
| C(1)—C(3) | 1.488(8) | C(18)—C(19) | 1.399(8) | N(1L)—C(1LC) | 1.15(3) |
| S(2)—C(29) | 1.823(6) | C(19)—C(20) | 1.402(10) | N(1L)—C(1LA) | 1.68(3) |
| S(2)—C(28) | 1.827(6) | C(20)—C(21) | 1.331(10) | N(1L)—O(10W) | 1.71(4) |
| N(2)—C(2) | 1.335(7) | C(21)—C(22) | 1.418(10) | N(1L)—C(2L) | 1.82(6) |
| O(2)—C(23) | 1.227(7) | C(24)—C(29) | 1.539(8) | C(1LA)—C(2LC) | 0.82(3) |
| C(2)—N(3) | 1.320(7) | C(24)—C(25) | 1.543(8) | C(1LA)—N(3L) | 1.15(2) |
| O(3)—C(25) | 1.201(6) | C(26)—C(27) | 1.362(7) | C(1LA)—C(5LD) | 1.49(5) |
| C(3)—N(4) | 1.286(7) | C(26)—C(30) | 1.476(7) | C(1LA)—C(3LD) | 1.55(5) |
| C(3)—C(23) | 1.529(7) | C(27)—C(44) | 1.485(8) | C(1LA)—C(2LB) | 1.58(3) |
| O(4)—C(30) | 1.226(7) | C(27)—C(28) | 1.521(9) | C(1LA)—C(2LD) | 1.59(5) |
| C(4)—C(11) | 1.516(9) | C(31)—C(38) | 1.386(10) | C(1LA)—C(2L) | 1.60(6) |
| C(4)—C(17) | 1.518(8) | C(31)—C(32) | 1.548(9) | C(1LC)—C(2L) | 1.17(6) |
| C(4)—C(5) | 1.544(8) | C(31)—C(38') | 1.907(17) | C(1LC)—N(2L) | 1.19(4) |
| O(5)—C(30) | 1.346(7) | C(32)—C(37) | 1.344(10) | C(1LC)—C(2LB) | 1.19(4) |
| O(5)—C(31) | 1.468(7) | C(32)—C(33) | 1.389(9) | C(1LC)—O(10W) | 1.76(5) |
| C(5)—C(6) | 1.394(8) | C(33)—C(34) | 1.412(10) | C(1LC)—N(3L) | 1.80(4) |
| C(5)—C(10) | 1.415(9) | C(34)—C(35) | 1.395(10) | C(1LC)—C(5LD) | 1.84(6) |
| N(5)—C(23) | 1.335(7) | C(35)—C(36) | 1.348(10) | C(2LB)—C(2L) | 1.31(6) |
| N(5)—C(24) | 1.439(6) | C(36)—C(37) | 1.418(11) | C(2LB)—N(2L) | 1.33(4) |
| O(6)—C(48) | 1.235(7) | C(38)—C(39) | 1.3900 | C(2LB)—N(3L) | 1.38(3) |
| N(6)—C(26) | 1.390(6) | C(38)—C(43) | 1.3900 | C(2LB)—C(2LC) | 1.49(4) |
| N(6)—C(25) | 1.427(6) | C(39)—C(40) | 1.3900 | C(2LB)—C(2LD) | 1.63(5) |
| N(6)—C(29) | 1.468(7) | C(40)—C(41) | 1.3900 | C(2LB)—C(5LD) | 1.84(5) |
| C(6)—C(7) | 1.386(9) | C(41)—C(42) | 1.3900 | C(2L)—C(5LD) | 0.73(6) |
| O(7)—C(53) | 1.232(8) | C(42)—C(43) | 1.3900 | C(2L)—C(2LC) | 1.23(6) |
| N(7)—C(48) | 1.370(7) | C(38')—C(39') | 1.3900 | C(2L)—C(2LD) | 1.69(7) |
| N(7)—C(47) | 1.463(8) | C(38')—C(43') | 1.3900 | C(2L)—C(3LD) | 1.88(8) |
| N(7)—C(49) | 1.470(6) | C(39')—C(40') | 1.3900 | N(2L)—N(3L) | 1.74(4) |
| C(7)—C(8) | 1.368(11) | C(40')—C(41') | 1.3900 | N(2L)—C(4LD) | 1.81(7) |
| O(8)—C(53) | 1.348(7) | C(41')—C(42') | 1.3900 | C(2LC)—C(2LD) | 0.90(4) |
| O(8)—C(54) | 1.494(9) | C(42')—C(43') | 1.3900 | C(2LC)—C(5LD) | 1.01(4) |
| N(8)—C(53) | 1.357(8) | C(44)—C(45) | 1.325(8) | C(2LC)—C(3LD) | 1.64(6) |
| N(8)—C(50) | 1.469(9) | C(45)—C(48) | 1.482(7) | C(2LC)—N(3L) | 1.77(4) |
| N(8)—C(51) | 1.483(7) | C(45)—C(46) | 1.509(9) | O(1W)—O(6W) | 0.82(2) |
| C(8)—C(9) | 1.390(11) | C(46)—C(47) | 1.554(8) | O(1W)—O(2W) | 1.19(2) |
| C(9)—C(10) | 1.427(8) | C(49)—C(50) | 1.526(9) | O(1W)—O(3W) | 1.68(3) |
| C(11)—C(12) | 1.398(8) | C(49)—C(52) | 1.543(9) | O(2W)—O(6W) | 1.13(2) |
| C(11)—C(16) | 1.412(8) | C(51)—C(52) | 1.523(9) | O(2W)—O(3W) | 1.57(3) |
| O(4W)—O(5W) | 1.47(4) | O(9W)—C(3LD)#1 | 1.87(7) | C(3LD)—O(9W)#1 | 1.87(7) |
| O(4W)—O(7W) | 1.80(5) | O(11W)—C(4LD)#2 | 1.79(8) | C(4LD)—O(11W)#3 | 1.79(8) |
| O(5W)—O(7W) | 1.24(4) | C(2LD)—C(5LD) | 1.62(6) | | |
| O(8W)—O(9W) | 1.27(4) | C(3LD)—C(5LD) | 1.32(6) | | |
| N(1)—S(1)—C(2) | | 91.7(2) | C(12)—C(11)—C(16) | | 118.1(6) |
| C(1)—N(1)—S(1) | | 107.2(4) | C(12)—C(11)—C(4) | | 122.4(5) |
| N(4)—O(1)—C(4) | | 115.2(3) | C(16)—C(11)—C(4) | | 119.5(5) |
| N(1)—C(1)—N(2) | | 120.9(5) | C(11)—C(12)—C(13) | | 121.3(6) |

TABLE 2-continued

Bond lengths [Ang] and angles [°] (cf. FIG. 3)

| | | | |
|---|---|---|---|
| N(1)—C(1)—C(3) | 119.0(4) | C(14)—C(13)—C(12) | 119.2(7) |
| N(2)—C(1)—C(3) | 120.0(5) | C(13)—C(14)—C(15) | 120.5(7) |
| C(29)—S(2)—C(28) | 92.4(3) | C(16)—C(15)—C(14) | 119.9(7) |
| C(2)—N(2)—C(1) | 109.0(4) | C(15)—C(16)—C(11) | 120.9(6) |
| N(3)—C(2)—N(2) | 124.9(5) | C(22)—C(17)—C(18) | 118.3(6) |
| N(3)—C(2)—S(1) | 123.8(4) | C(22)—C(17)—C(4) | 121.4(5) |
| N(2)—C(2)—S(1) | 111.3(4) | C(18)—C(17)—C(4) | 120.3(5) |
| N(4)—C(3)—C(1) | 118.4(4) | C(19)—C(18)—C(17) | 120.8(6) |
| N(4)—C(3)—C(23) | 123.3(4) | C(18)—C(19)—C(20) | 119.3(6) |
| C(1)—C(3)—C(23) | 118.1(4) | C(21)—C(20)—C(19) | 120.1(6) |
| C(3)—N(4)—O(1) | 110.3(4) | C(20)—C(21)—C(22) | 121.4(7) |
| O(1)—C(4)—C(11) | 108.0(5) | C(17)—C(22)—C(21) | 120.1(6) |
| O(1)—C(4)—C(17) | 110.8(4) | O(2)—C(23)—N(5) | 124.4(5) |
| C(11)—C(4)—C(17) | 111.7(4) | O(2)—C(23)—C(3) | 117.8(5) |
| O(1)—C(4)—C(5) | 101.2(4) | N(5)—C(23)—C(3) | 117.8(5) |
| C(11)—C(4)—C(5) | 112.9(5) | N(5)—C(24)—C(29) | 120.3(5) |
| C(17)—C(4)—C(5) | 111.7(5) | N(5)—C(24)—C(25) | 118.8(5) |
| C(30)—O(5)—C(31) | 116.4(5) | C(29)—C(24)—C(25) | 86.4(4) |
| C(6)—C(5)—C(10) | 118.5(5) | O(3)—C(25)—N(6) | 132.8(5) |
| C(6)—C(5)—C(4) | 120.4(5) | O(3)—C(25)—C(24) | 137.8(5) |
| C(10)—C(5)—C(4) | 121.1(5) | N(6)—C(25)—C(24) | 89.4(4) |
| C(23)—N(5)—C(24) | 117.1(5) | C(27)—C(26)—N(6) | 118.6(5) |
| C(26)—N(6)—C(25) | 135.4(4) | C(27)—C(26)—C(30) | 123.7(5) |
| C(26)—N(6)—C(29) | 124.8(4) | N(6)—C(26)—C(30) | 117.6(4) |
| C(25)—N(6)—C(29) | 93.5(4) | C(26)—C(27)—C(44) | 124.6(5) |
| C(7)—C(6)—C(5) | 120.5(6) | C(26)—C(27)—C(28) | 125.1(5) |
| C(48)—N(7)—C(47) | 113.6(4) | C(44)—C(27)—C(28) | 109.5(5) |
| C(48)—N(7)—C(49) | 122.3(5) | C(27)—C(28)—S(2) | 115.6(4) |
| C(47)—N(7)—C(49) | 123.9(5) | N(6)—C(29)—C(24) | 88.0(4) |
| C(8)—C(7)—C(6) | 121.4(6) | N(6)—C(29)—S(2) | 109.8(4) |
| C(53)—O(8)—C(54) | 120.8(6) | C(24)—C(29)—S(2) | 117.2(4) |
| C(53)—N(8)—C(50) | 125.7(5) | O(4)—C(30)—O(5) | 122.7(5) |
| C(53)—N(8)—C(51) | 123.0(5) | O(4)—C(30)—C(26) | 122.1(5) |
| C(50)—N(8)—C(51) | 110.9(5) | O(5)—C(30)—C(26) | 115.2(4) |
| C(7)—C(8)—C(9) | 120.8(6) | C(38)—C(31)—O(5) | 111.4(7) |
| C(8)—C(9)—C(10) | 118.5(7) | C(38)—C(31)—C(32) | 114.4(7) |
| C(5)—C(10)—C(9) | 120.4(6) | O(5)—C(31)—C(32) | 111.9(5) |
| C(38)—C(31)—C(38') | 26.5(7) | C(55)—C(54)—C(56) | 112.0(7) |
| O(5)—C(31)—C(38') | 99.1(6) | O(8)—C(54)—C(57) | 109.2(6) |
| C(32)—C(31)—C(38') | 100.3(7) | C(55)—C(54)—C(57) | 113.4(9) |
| C(37)—C(32)—C(33) | 119.1(6) | C(56)—C(54)—C(57) | 108.2(7) |
| C(37)—C(32)—C(31) | 118.8(6) | N(3L)—N(1L)—N(2L) | 151(4) |
| C(33)—C(32)—C(31) | 121.8(6) | N(3L)—N(1L)—C(2LB) | 90(2) |
| C(32)—C(33)—C(34) | 119.4(6) | N(2L)—N(1L)—C(2LB) | 79(3) |
| C(35)—C(34)—C(33) | 120.1(6) | N(3L)—N(1L)—C(1LC) | 131(3) |
| C(36)—C(35)—C(34) | 119.7(6) | N(2L)—N(1L)—C(1LC) | 68(3) |
| C(35)—C(36)—C(37) | 119.4(7) | C(2LB)—N(1L)—C(1LC) | 64(2) |
| C(32)—C(37)—C(36) | 122.0(7) | N(3L)—N(1L)—C(1LA) | 38.5(17) |
| C(31)—C(38)—C(39) | 116.6(8) | N(2L)—N(1L)—C(1LA) | 144(2) |
| C(31)—C(38)—C(43) | 123.0(8) | C(2LB)—N(1L)—C(1LA) | 65.3(18) |
| C(39)—C(38)—C(43) | 120.0 | C(1LC)—N(1L)—C(1LA) | 92(2) |
| C(40)—C(39)—C(38) | 120.0 | N(3L)—N(1L)—O(10W) | 97(2) |
| C(39)—C(40)—C(41) | 120.0 | N(2L)—N(1L)—O(10W) | 111(3) |
| C(42)—C(41)—C(40) | 120.0 | C(2LB)—N(1L)—O(10W) | 127(2) |
| C(43)—C(42)—C(41) | 120.0 | C(1LC)—N(1L)—O(10W) | 73(2) |
| C(42)—C(43)—C(38) | 120.0 | C(1LA)—N(1L)—O(10W) | 89.2(16) |
| C(39')—C(38')—C(43') | 120.0 | N(3L)—N(1L)—C(2L) | 93(3) |
| C(39')—C(38')—C(31) | 125.9(8) | N(2L)—N(1L)—C(2L) | 98(3) |
| C(43')—C(38')—C(31) | 114.1(8) | C(2LB)—N(1L)—C(2L) | 45(2) |
| C(40')—C(39')—C(38') | 120.0 | C(1LC)—N(1L)—C(2L) | 39(2) |
| C(39')—C(40')—C(41') | 120.0 | C(1LA)—N(1L)—C(2L) | 54(2) |
| C(40')—C(41')—C(42') | 120.0 | O(10W)—N(1L)—C(2L) | 82(2) |
| C(43')—C(42')—C(41') | 120.0 | C(2LC)—C(1LA)—N(3L) | 127(3) |
| C(42')—C(43')—C(38') | 120.0 | C(2LC)—C(1LA)—C(5LD) | 41(3) |
| C(45)—C(44)—C(27) | 125.7(6) | N(3L)—C(1LA)—C(5LD) | 120(3) |
| C(44)—C(45)—C(48) | 121.8(5) | C(2LC)—C(1LA)—C(3LD) | 81(3) |
| C(44)—C(45)—C(46) | 128.9(5) | N(3L)—C(1LA)—C(3LD) | 129(3) |
| C(48)—C(45)—C(46) | 109.3(5) | C(5LD)—C(1LA)—C(3LD) | 52(2) |
| C(45)—C(46)—C(47) | 102.3(5) | C(2LC)—C(1LA)—C(2LB) | 69(3) |
| N(7)—C(47)—C(46) | 105.0(5) | N(3L)—C(1LA)—C(2LB) | 58.3(16) |
| O(6)—C(48)—N(7) | 124.9(5) | C(5LD)—C(1LA)—C(2LB) | 74(2) |
| O(6)—C(48)—C(45) | 128.3(5) | C(3LD)—C(1LA)—C(2LB) | 121(2) |
| N(7)—C(48)—C(45) | 106.9(5) | C(2LC)—C(1LA)—C(2LD) | 24(3) |
| N(7)—C(49)—C(50) | 110.8(5) | N(3L)—C(1LA)—C(2LD) | 114(2) |
| N(7)—C(49)—C(52) | 113.0(4) | C(5LD)—C(1LA)—C(2LD) | 64(3) |
| C(50)—C(49)—C(52) | 103.2(5) | C(3LD)—C(1LA)—C(2LD) | 104(3) |
| N(8)—C(50)—C(49) | 104.3(5) | C(2LB)—C(1LA)—C(2LD) | 62(2) |
| N(8)—C(51)—C(52) | 105.1(5) | C(2LC)—C(1LA)—C(2L) | 49(3) |

TABLE 2-continued

Bond lengths [Ang] and angles [°] (cf. FIG. 3)

| | | | |
|---|---|---|---|
| C(51)—C(52)—C(49) | 105.2(5) | N(3L)—C(1LA)—C(2L) | 94(3) |
| O(7)—C(53)—O(8) | 125.4(6) | C(5LD)—C(1LA)—C(2L) | 27(2) |
| O(7)—C(53)—N(8) | 122.9(5) | C(3LD)—C(1LA)—C(2L) | 73(3) |
| O(8)—C(53)—N(8) | 111.7(6) | C(2LB)—C(1LA)—C(2L) | 49(2) |
| O(8)—C(54)—C(55) | 110.9(7) | C(2LD)—C(1LA)—C(2L) | 64(3) |
| O(8)—C(54)—C(56) | 102.5(7) | C(2LC)—C(1LA)—N(1L) | 106(3) |
| N(3L)—C(1LA)—N(1L) | 26.3(11) | C(2LC)—C(2LB)—C(1LA) | 31.0(13) |
| C(5LD)—C(1LA)—N(1L) | 93(2) | N(1L)—C(2LB)—C(2LD) | 134(3) |
| C(3LD)—C(1LA)—N(1L) | 116(2) | C(1LC)—C(2LB)—C(2LD) | 125(3) |
| C(2LB)—C(1LA)—N(1L) | 39.8(12) | C(2L)—C(2LB)—C(2LD) | 70(3) |
| C(2LD)—C(1LA)—N(1L) | 101(2) | N(2L)—C(2LB)—C(2LD) | 179(3) |
| C(2L)—C(1LA)—N(1L) | 68(2) | N(3L)—C(2LB)—C(2LD) | 100(2) |
| N(1L)—C(1LC)—C(2L) | 104(4) | C(2LC)—C(2LB)—C(2LD) | 33.3(17) |
| N(1L)—C(1LC)—N(2L) | 49(2) | C(1LA)—C(2LB)—C(2LD) | 59(2) |
| C(2L)—C(1LC)—N(2L) | 135(4) | N(1L)—C(2LB)—C(5LD) | 100(2) |
| N(1L)—C(1LC)—C(2LB) | 57(2) | C(1LC)—C(2LB)—C(5LD) | 71(2) |
| C(2L)—C(1LC)—C(2LB) | 67(3) | C(2L)—C(2LB)—C(5LD) | 19(3) |
| N(2L)—C(1LC)—C(2LB) | 68(3) | N(2L)—C(2LB)—C(5LD) | 126(3) |
| N(1L)—C(1LC)—O(10W) | 69(2) | N(3L)—C(2LB)—C(5LD) | 89.2(19) |
| C(2L)—C(1LC)—O(10W) | 103(4) | C(2LC)—C(2LB)—C(5LD) | 33.3(16) |
| N(2L)—C(1LC)—O(10W) | 98(3) | C(1LA)—C(2LB)—C(5LD) | 50.7(17) |
| C(2LB)—C(1LC)—O(10W) | 118(3) | C(2LD)—C(2LB)—C(5LD) | 55(2) |
| N(1L)—C(1LC)—N(3L) | 20.3(13) | C(5LD)—C(2L)—C(1LC) | 149(8) |
| C(2L)—C(1LC)—N(3L) | 84(3) | C(5LD)—C(2L)—C(2LC) | 55(5) |
| N(2L)—C(1LC)—N(3L) | 68(3) | C(1LC)—C(2L)—C(2LC) | 120(5) |
| C(2LB)—C(1LC)—N(3L) | 50.1(18) | C(5LD)—C(2L)—C(2LB) | 127(7) |
| O(10W)—C(1LC)—N(3L) | 68.1(17) | C(1LC)—C(2L)—C(2LB) | 57(3) |
| N(1L)—C(1LC)—C(5LD) | 98(3) | C(2LC)—C(2L)—C(2LB) | 72(3) |
| C(2L)—C(1LC)—C(5LD) | 12(3) | C(5LD)—C(2L)—C(1LA) | 67(6) |
| N(2L)—C(1LC)—C(5LD) | 138(3) | C(1LC)—C(2L)—C(1LA) | 95(4) |
| C(2LB)—C(1LC)—C(5LD) | 71(2) | C(2LC)—C(2L)—C(1LA) | 30(2) |
| O(10W)—C(1LC)—C(5LD) | 91(2) | C(2LB)—C(2L)—C(1LA) | 65(3) |
| N(3L)—C(1LC)—C(5LD) | 78.0(18) | C(5LD)—C(2L)—C(2LD) | 72(6) |
| N(1L)—C(2LB)—C(1LC) | 60(2) | C(1LC)—C(2L)—C(2LD) | 121(5) |
| N(1L)—C(2LB)—C(2L) | 98(3) | C(2LC)—C(2L)—C(2LD) | 31(2) |
| C(1LC)—C(2LB)—C(2L) | 56(3) | C(2LB)—C(2L)—C(2LD) | 64(3) |
| N(1L)—C(2LB)—N(2L) | 45.8(19) | C(1LA)—C(2L)—C(2LD) | 58(3) |
| C(1LC)—C(2LB)—N(2L) | 56(2) | C(5LD)—C(2L)—N(1L) | 123(7) |
| C(2L)—C(2LB)—N(2L) | 112(4) | C(1LC)—C(2L)—N(1L) | 38(2) |
| N(1L)—C(2LB)—N(3L) | 36.6(13) | C(2LC)—C(2L)—N(1L) | 82(3) |
| C(1LC)—C(2LB)—N(3L) | 88(2) | C(2LB)—C(2L)—N(1L) | 37.1(19) |
| C(2L)—C(2LB)—N(3L) | 99(3) | C(1LA)—C(2L)—N(1L) | 58(2) |
| N(2L)—C(2LB)—N(3L) | 80(2) | C(2LD)—C(2L)—N(1L) | 92(3) |
| N(1L)—C(2LB)—C(2LC) | 104(3) | C(5LD)—C(2L)—C(3LD) | 32(5) |
| C(1LC)—C(2LB)—C(2LC) | 101(3) | C(1LC)—C(2L)—C(3LD) | 117(4) |
| C(2L)—C(2LB)—C(2LC) | 52(3) | C(2LC)—C(2L)—C(3LD) | 59(3) |
| N(2L)—C(2LB)—C(2LC) | 147(3) | C(2LB)—C(2L)—C(3LD) | 116(4) |
| N(3L)—C(2LB)—C(2LC) | 76.3(19) | C(1LA)—C(2L)—C(3LD) | 52(2) |
| N(1L)—C(2LB)—C(1LA) | 75(2) | C(2LD)—C(2L)—C(3LD) | 88(4) |
| C(1LC)—C(2LB)—C(1LA) | 96(2) | N(1L)—C(2L)—C(3LD) | 95(3) |
| C(2L)—C(2LB)—C(1LA) | 67(3) | N(1L)—N(2L)—C(1LC) | 63(3) |
| N(2L)—C(2LB)—C(1LA) | 121(3) | N(1L)—N(2L)—C(2LB) | 55(2) |
| N(3L)—C(2LB)—C(1LA) | 45.3(13) | C(1LC)—N(2L)—C(2LB) | 56(2) |
| N(1L)—N(2L)—N(3L) | 13.2(16) | O(6W)—O(2W)—O(3W) | 113(2) |
| C(1LC)—N(2L)—N(3L) | 73(3) | O(1W)—O(2W)—O(3W) | 73.5(16) |
| C(2LB)—N(2L)—N(3L) | 51.4(19) | O(2W)—O(3W)—O(1W) | 42.9(10) |
| N(1L)—N(2L)—C(4LD) | 148(4) | O(5W)—O(4W)—O(7W) | 43.3(15) |
| C(1LC)—N(2L)—C(4LD) | 86(3) | O(1W)—O(6W)—O(2W) | 74(2) |
| C(2LB)—N(2L)—C(4LD) | 115(3) | O(7W)—O(5W)—O(4W) | 83(2) |
| N(3L)—N(2L)—C(4LD) | 159(3) | O(5W)—O(7W)—O(4W) | 54.2(19) |
| C(1LA)—C(2LC)—C(2LD) | 134(6) | O(8W)—O(9W)—C(3LD)#1 | 171(4) |
| C(1LA)—C(2LC)—C(5LD) | 107(5) | N(1L)—O(10W)—C(1LC) | 38.7(13) |
| C(2LD)—C(2LC)—C(5LD) | 116(5) | C(2LC)—C(2LD)—C(1LA) | 22(3) |
| C(1LA)—C(2LC)—C(2L) | 101(4) | C(2LC)—C(2LD)—C(5LD) | 34(3) |
| C(2LD)—C(2LC)—C(2L) | 104(5) | C(1LA)—C(2LD)—C(5LD) | 55(2) |
| C(5LD)—C(2LC)—C(2L) | 37(3) | C(2LC)—C(2LD)—C(2LB) | 65(3) |
| C(1LA)—C(2LC)—C(2LB) | 80(3) | C(1LA)—C(2LD)—C(2LB) | 59(2) |
| C(2LD)—C(2LC)—C(2LB) | 82(4) | C(5LD)—C(2LD)—C(2LB) | 69(3) |
| C(5LD)—C(2LC)—C(2LB) | 93(3) | C(2LC)—C(2LD)—C(2L) | 45(3) |
| C(2L)—C(2LC)—C(2LB) | 57(3) | C(1LA)—C(2LD)—C(2L) | 58(3) |
| C(1LA)—C(2LC)—C(3LD) | 69(3) | C(5LD)—C(2LD)—C(2L) | 25(2) |
| C(2LD)—C(2LC)—C(3LD) | 153(5) | C(2LB)—C(2LD)—C(2L) | 46(2) |
| C(5LD)—C(2LC)—C(3LD) | 54(3) | C(5LD)—C(3LD)—C(1LA) | 62(3) |
| C(2L)—C(2LC)—C(3LD) | 80(4) | C(5LD)—C(3LD)—C(2LC) | 38(2) |
| C(2LB)—C(2LC)—C(3LD) | 121(3) | C(1LA)—C(3LD)—C(2LC) | 29.8(14) |
| C(1LA)—C(2LC)—N(3L) | 31(2) | C(5LD)—C(3LD)—O(9W)#1 | 134(4) |
| C(2LD)—C(2LC)—N(3L) | 115(4) | C(1LA)—C(3LD)—O(9W)#1 | 146(4) |
| C(5LD)—C(2LC)—N(3L) | 107(3) | C(2LC)—C(3LD)—O(9W)#1 | 139(3) |

TABLE 2-continued

Bond lengths [Ang] and angles [°] (cf. FIG. 3)

| | | | |
|---|---|---|---|
| C(2L)—C(2LC)—N(3L) | 83(3) | C(5LD)—C(3LD)—C(2L) | 17(3) |
| C(2LB)—C(2LC)—N(3L) | 49.1(15) | C(1LA)—C(3LD)—C(2L) | 55(2) |
| C(3LD)—C(2LC)—N(3L) | 91(2) | C(2LC)—C(3LD)—C(2L) | 40(2) |
| N(1L)—N(3L)—C(1LA) | 115(2) | O(9W)#1—C(3LD)—C(2L) | 150(4) |
| N(1L)—N(3L)—C(2LB) | 53.6(19) | O(11W)#3—C(4LD)—N(2L) | 138(4) |
| C(1LA)—N(3L)—C(2LB) | 76.4(18) | C(2L)—C(5LD)—C(2LC) | 88(6) |
| N(1L)—N(3L)—N(2L) | 15.7(19) | C(2L)—C(5LD)—C(3LD) | 130(7) |
| C(1LA)—N(3L)—N(2L) | 121(2) | C(2LC)—C(5LD)—C(3LD) | 88(4) |
| C(2LB)—N(3L)—N(2L) | 48.9(16) | C(2L)—C(5LD)—C(1LA) | 85(6) |
| N(1L)—N(3L)—C(2LC) | 98(2) | C(2LC)—C(5LD)—C(1LA) | 32(2) |
| C(1LA)—N(3L)—C(2LC) | 21.9(14) | C(3LD)—C(5LD)—C(1LA) | 67(3) |
| C(2LB)—N(3L)—C(2LC) | 54.7(16) | C(2L)—C(5LD)—C(2LD) | 83(6) |
| N(2L)—N(3L)—C(2LC) | 100.8(18) | C(2LC)—C(5LD)—C(2LD) | 30(3) |
| N(1L)—N(3L)—C(1LC) | 29.1(19) | C(3LD)—C(5LD)—C(2LD) | 114(4) |
| C(1LA)—N(3L)—C(1LC) | 86.2(17) | C(1LA)—C(5LD)—C(2LD) | 61(3) |
| C(2LB)—N(3L)—C(1LC) | 41.6(14) | C(2L)—C(5LD)—C(1LC) | 19(5) |
| N(2L)—N(3L)—C(1LC) | 39.3(15) | C(2LC)—C(5LD)—C(1LC) | 89(3) |
| C(2LC)—N(3L)—C(1LC) | 71.3(15) | C(3LD)—C(5LD)—C(1LC) | 111(3) |
| O(6W)—O(1W)—O(2W) | 65(2) | C(1LA)—C(5LD)—C(1LC) | 76(2) |
| O(6W)—O(1W)—O(3W) | 127(2) | C(2LD)—C(5LD)—C(1LC) | 93(3) |
| O(2W)—O(1W)—O(3W) | 63.6(14) | C(2L)—C(5LD)—C(2LB) | 34(5) |
| O(6W)—O(2W)—O(1W) | 41.2(13) | C(2LC)—C(5LD)—C(2LB) | 54(3) |
| C(3LD)—C(5LD)—C(2LB) | 117(4) | C(2LD)—C(5LD)—C(2LB) | 55(2) |
| C(1LA)—C(5LD)—C(2LB) | 55.3(18) | C(1LC)—C(5LD)—C(2LB) | 37.8(15) |

Symmetry transformations used to generate equivalent atoms:
1 −x+1,y,−z+1   #2 −x+1,y−1,−z+1   #3 −x+1,y+1,−z+1

TABLE 3

Torsion angles [°] (cf. FIG. 4)

| | | | |
|---|---|---|---|
| C(2)—S(1)—N(1)—C(1) | −0.3(5) | C(4)—C(11)—C(12)—C(13) | 179.5(6) |
| S(1)—N(1)—C(1)—N(2) | −0.1(8) | C(11)—C(12)—C(13)—C(14) | 1.1(10) |
| S(1)—N(1)—C(1)—C(3) | −175.6(5) | C(12)—C(13)—C(14)—C(15) | −2.3(11) |
| N(1)—C(1)—N(2)—C(2) | 0.6(8) | C(13)—C(14)—C(15)—C(16) | 2.9(11) |
| C(3)—C(1)—N(2)—C(2) | 176.0(6) | C(14)—C(15)—C(16)—C(11) | −2.1(10) |
| C(1)—N(2)—C(2)—N(3) | 178.5(7) | C(12)—C(11)—C(16)—C(15) | 0.8(8) |
| C(1)—N(2)—C(2)—S(1) | −0.7(7) | C(4)—C(11)—C(16)—C(15) | −179.0(5) |
| N(1)—S(1)—C(2)—N(3) | −178.7(6) | O(1)—C(4)—C(17)—C(22) | −36.4(7) |
| N(1)—S(1)—C(2)—N(2) | 0.6(5) | C(11)—C(4)—C(17)—C(22) | −156.9(5) |
| N(1)—C(1)—C(3)—N(4) | 167.3(6) | C(5)—C(4)—C(17)—C(22) | 75.6(6) |
| N(2)—C(1)—C(3)—N(4) | −8.3(9) | O(1)—C(4)—C(17)—C(18) | 145.2(5) |
| N(1)—C(1)—C(3)—C(23) | −18.2(9) | C(11)—C(4)—C(17)—C(18) | 24.8(7) |
| N(2)—C(1)—C(3)—C(23) | 166.2(5) | C(5)—C(4)—C(17)—C(18) | −102.7(6) |
| C(1)—C(3)—N(4)—O(1) | −176.3(5) | C(22)—C(17)—C(18)—C(19) | 0.7(8) |
| C(23)—C(3)—N(4)—O(1) | 9.6(8) | C(4)—C(17)—C(18)—C(19) | 179.1(5) |
| C(4)—O(1)—N(4)—C(3) | −175.7(5) | C(17)—C(18)—C(19)—C(20) | 1.1(8) |
| N(4)—O(1)—C(4)—C(11) | 82.8(5) | C(18)—C(19)—C(20)—C(21) | −1.9(9) |
| N(4)—O(1)—C(4)—C(17) | −39.8(6) | C(19)—C(20)—C(21)—C(22) | 0.8(10) |
| N(4)—O(1)—C(4)—C(5) | −158.5(5) | C(18)—C(17)—C(22)—C(21) | −1.8(8) |
| O(1)—C(4)—C(5)—C(6) | −37.2(7) | C(4)—C(17)—C(22)—C(21) | 179.8(5) |
| C(11)—C(4)—C(5)—C(6) | 77.9(6) | C(20)—C(21)—C(22)—C(17) | 1.1(10) |
| C(17)—C(4)—C(5)—C(6) | −155.2(5) | C(24)—N(5)—C(23)—O(2) | −3.5(8) |
| O(1)—C(4)—C(5)—C(10) | 140.1(5) | C(24)—N(5)—C(23)—C(3) | 177.3(5) |
| C(11)—C(4)—C(5)—C(10) | −104.8(6) | N(4)—C(3)—C(23)—O(2) | 103.8(7) |
| C(17)—C(4)—C(5)—C(10) | 22.1(7) | C(1)—C(3)—C(23)—O(2) | −70.4(7) |
| C(10)—C(5)—C(6)—C(7) | 0.5(9) | N(4)—C(3)—C(23)—N(5) | −76.9(7) |
| C(4)—C(5)—C(6)—C(7) | 177.9(5) | C(1)—C(3)—C(23)—N(5) | 108.9(6) |
| C(5)—C(6)—C(7)—C(8) | 0.1(10) | C(23)—N(5)—C(24)—C(29) | 95.1(6) |
| C(6)—C(7)—C(8)—C(9) | 0.7(11) | C(23)—N(5)—C(24)—C(25) | −161.1(5) |
| C(7)—C(8)—C(9)—C(10) | −2.0(11) | C(26)—N(6)—C(25)—O(3) | −16.3(10) |
| C(6)—C(5)—C(10)—C(9) | −1.8(9) | C(29)—N(6)—C(25)—O(3) | −167.5(6) |
| C(4)—C(5)—C(10)—C(9) | −179.2(6) | C(26)—N(6)—C(25)—C(24) | 163.8(5) |
| C(8)—C(9)—C(10)—C(5) | 2.6(10) | C(29)—N(6)—C(25)—C(24) | 12.7(4) |
| O(1)—C(4)—C(11)—C(12) | 125.3(5) | N(5)—C(24)—C(25)—O(3) | 45.2(9) |
| C(17)—C(4)—C(11)—C(12) | −112.6(5) | C(29)—C(24)—C(25)—O(3) | 168.1(7) |
| C(5)—C(4)—C(11)—C(12) | 14.3(7) | N(5)—C(24)—C(25)—N(6) | −135.0(5) |
| O(1)—C(4)—C(11)—C(16) | −54.9(6) | C(29)—C(24)—C(25)—N(6) | −12.1(4) |
| C(17)—C(4)—C(11)—C(16) | 67.2(6) | C(25)—N(6)—C(26)—C(27) | −135.6(6) |
| C(5)—C(4)—C(11)—C(16) | −165.9(5) | C(29)—N(6)—C(26)—C(27) | 8.5(7) |
| C(16)—C(11)—C(12)—C(13) | −0.3(8) | C(25)—N(6)—C(26)—C(30) | 47.3(7) |
| C(29)—N(6)—C(26)—C(30) | −168.6(5) | C(40)—C(41)—C(42)—C(43) | 0.0 |
| N(6)—C(26)—C(27)—C(44) | −159.0(6) | C(41)—C(42)—C(43)—C(38) | 0.0 |

TABLE 3-continued

Torsion angles [°] (cf. FIG. 4)

| | | | |
|---|---|---|---|
| C(30)—C(26)—C(27)—C(44) | 17.9(9) | C(31)—C(38)—C(43)—C(42) | 172.8(9) |
| N(6)—C(26)—C(27)—C(28) | 9.9(9) | C(39)—C(38)—C(43)—C(42) | 0.0 |
| C(30)—C(26)—C(27)—C(28) | −173.2(6) | C(38)—C(31)—C(38′)—C(39′) | −149(2) |
| C(26)—C(27)—C(28)—S(2) | 17.0(10) | O(5)—C(31)—C(38′)—C(39′) | −28.1(14) |
| C(44)—C(27)—C(28)—S(2) | −172.7(6) | C(32)—C(31)—C(38′)—C(39′) | 86.4(14) |
| C(29)—S(2)—C(28)—C(27) | −46.7(7) | C(38)—C(31)—C(38′)—C(43′) | 30.3(14) |
| C(26)—N(6)—C(29)—C(24) | −168.3(5) | O(5)—C(31)—C(38′)—C(43′) | 150.8(9) |
| C(25)—N(6)—C(29)—C(24) | −12.7(4) | C(32)—C(31)—C(38′)—C(43′) | −94.7(10) |
| C(26)—N(6)—C(29)—S(2) | −50.1(6) | C(43′)—C(38′)—C(39′)—C(40′) | 0.0 |
| C(25)—N(6)—C(29)—S(2) | 105.6(4) | C(31)—C(38′)—C(39′)—C(40′) | 178.8(15) |
| N(5)—C(24)—C(29)—N(6) | 133.2(5) | C(38′)—C(39′)—C(40′)—C(41′) | 0.0 |
| C(25)—C(24)—C(29)—N(6) | 11.8(4) | C(39′)—C(40′)—C(41′)—C(42′) | 0.0 |
| N(5)—C(24)—C(29)—S(2) | 21.9(7) | C(40′)—C(41′)—C(42′)—C(43′) | 0.0 |
| C(25)—C(24)—C(29)—S(2) | −99.5(4) | C(41′)—C(42′)—C(43′)—C(38′) | 0.0 |
| C(28)—S(2)—C(29)—N(6) | 60.2(5) | C(39′)—C(38′)—C(43′)—C(42′) | 0.0 |
| C(28)—S(2)—C(29)—C(24) | 158.5(5) | C(31)—C(38′)—C(43′)—C(42′) | −179.0(14) |
| C(31)—O(5)—C(30)—O(4) | −2.8(7) | C(26)—C(27)—C(44)—C(45) | 49.5(10) |
| C(31)—O(5)—C(30)—C(26) | 177.9(4) | C(28)—C(27)—C(44)—C(45) | −120.8(7) |
| C(27)—C(26)—C(30)—O(4) | 29.4(8) | C(27)—C(44)—C(45)—C(48) | 167.6(6) |
| N(6)—C(26)—C(30)—O(4) | −153.7(5) | C(27)—C(44)—C(45)—C(46) | −8.8(11) |
| C(27)—C(26)—C(30)—O(5) | −151.4(5) | C(44)—C(45)—C(46)—C(47) | 160.2(6) |
| N(6)—C(26)—C(30)—O(5) | 25.6(6) | C(48)—C(45)—C(46)—C(47) | −16.6(7) |
| C(30)—O(5)—C(31)—C(38) | −160.8(8) | C(48)—N(7)—C(47)—C(46) | −10.9(8) |
| C(30)—O(5)—C(31)—C(32) | 69.7(7) | C(49)—N(7)—C(47)—C(46) | 174.1(5) |
| C(30)—O(5)—C(31)—C(38′) | 174.8(7) | C(45)—C(46)—C(47)—N(7) | 16.1(7) |
| C(38)—C(31)—C(32)—C(37) | 72.3(12) | C(47)—N(7)—C(48)—O(6) | −178.1(6) |
| O(5)—C(31)—C(32)—C(37) | −159.8(8) | C(49)—N(7)—C(48)—O(6) | −3.0(8) |
| C(38′)—C(31)—C(32)—C(37) | 95.9(9) | C(47)—N(7)—C(48)—C(45) | 0.4(8) |
| C(38)—C(31)—C(32)—C(33) | −102.0(10) | C(49)—N(7)—C(48)—C(45) | 175.5(5) |
| O(5)—C(31)—C(32)—C(33) | 25.9(10) | C(44)—C(45)—C(48)—O(6) | 12.2(9) |
| C(38′)—C(31)—C(32)—C(33) | −78.3(8) | C(46)—C(45)—C(48)—O(6) | −170.8(6) |
| C(37)—C(32)—C(33)—C(34) | 4.7(11) | C(44)—C(45)—C(48)—N(7) | −166.2(5) |
| C(31)—C(32)—C(33)—C(34) | 178.9(6) | C(46)—C(45)—C(48)—N(7) | 10.8(6) |
| C(32)—C(33)—C(34)—C(35) | −3.2(10) | C(48)—N(7)—C(49)—C(50) | 122.8(6) |
| C(33)—C(34)—C(35)—C(36) | −1.0(11) | C(47)—N(7)—C(49)—C(50) | −62.6(7) |
| C(34)—C(35)—C(36)—C(37) | 3.5(13) | C(48)—N(7)—C(49)—C(52) | −121.9(6) |
| C(33)—C(32)—C(37)—C(36) | −2.2(13) | C(47)—N(7)—C(49)—C(52) | 52.7(8) |
| C(31)—C(32)—C(37)—C(36) | −176.6(8) | C(53)—N(8)—C(50)—C(49) | −150.7(5) |
| C(35)—C(36)—C(37)—C(32) | −2.0(15) | C(51)—N(8)—C(50)—C(49) | 21.6(6) |
| O(5)—C(31)—C(38)—C(39) | −55.5(9) | N(7)—C(49)—C(50)—N(8) | 88.8(6) |
| C(32)—C(31)—C(38)—C(39) | 72.7(8) | C(52)—C(49)—C(50)—N(8) | −32.4(6) |
| C(38′)—C(31)—C(38)—C(39) | 10.5(16) | C(53)—N(8)—C(51)—C(52) | 171.1(5) |
| O(5)—C(31)—C(38)—C(43) | 131.4(8) | C(50)—N(8)—C(51)—C(52) | −1.4(6) |
| C(32)—C(31)—C(38)—C(43) | −100.2(8) | N(8)—C(51)—C(52)—C(49) | −19.2(5) |
| C(38′)—C(31)—C(38)—C(43) | −163(2) | N(7)—C(49)—C(52)—C(51) | −87.8(6) |
| C(31)—C(38)—C(39)—C(40) | −173.3(8) | C(50)—C(49)—C(52)—C(51) | 32.0(5) |
| C(43)—C(38)—C(39)—C(40) | 0.0 | C(54)—O(8)—C(53)—O(7) | −3.7(9) |
| C(38)—C(39)—C(40)—C(41) | 0.0 | C(54)—O(8)—C(53)—N(8) | 177.0(5) |
| C(39)—C(40)—C(41)—C(42) | 0.0 | C(50)—N(8)—C(53)—O(7) | 170.1(5) |
| C(51)—N(8)—C(53)—O(7) | −1.3(8) | C(2LB)—N(1L)—C(1LC)—N(2L) | −89(3) |
| C(50)—N(8)—C(53)—O(8) | −10.7(8) | C(1LA)—N(1L)—C(1LC)—N(2L) | −150(3) |
| C(51)—N(8)—C(53)—O(8) | 177.9(5) | O(10W)—N(1L)—C(1LC)—N(2L) | 122(3) |
| C(53)—O(8)—C(54)—C(55) | 64.0(8) | C(2L)—N(1L)—C(1LC)—N(2L) | −139(4) |
| C(53)—O(8)—C(54)—C(56) | −176.4(6) | N(3L)—N(1L)—C(1LC)—C(2LB) | −65(4) |
| C(53)—O(8)—C(54)—C(57) | −61.8(8) | N(2L)—N(1L)—C(1LC)—C(2LB) | 89(3) |
| N(3L)—N(1L)—C(1LA)—C(2LC) | −145(4) | C(1LA)—N(1L)—C(1LC)—C(2LB) | −61(2) |
| N(2L)—N(1L)—C(1LA)—C(2LC) | −14(6) | O(10W)—N(1L)—C(1LC)—C(2LB) | −149(3) |
| C(2LB)—N(1L)—C(1LA)—C(2LC) | −21(3) | C(2L)—N(1L)—C(1LC)—C(2LB) | −50(4) |
| C(1LC)—N(1L)—C(1LA)—C(2LC) | 39(4) | N(3L)—N(1L)—C(1LC)—O(10W) | 85(4) |
| O(10W)—N(1L)—C(1LA)—C(2LC) | 112(3) | N(2L)—N(1L)—C(1LC)—O(10W) | −122(3) |
| C(2L)—N(1L)—C(1LA)—C(2LC) | 31(4) | C(2LB)—N(1L)—C(1LC)—O(10W) | 149(3) |
| N(2L)—N(1L)—C(1LA)—N(3L) | 131(6) | C(1LA)—N(1L)—C(1LC)—O(10W) | 88.4(17) |
| C(2LB)—N(1L)—C(1LA)—N(3L) | 125(3) | C(2L)—N(1L)—C(1LC)—O(10W) | 99(4) |
| C(1LC)—N(1L)—C(1LA)—N(3L) | −175(4) | N(2L)—N(1L)—C(1LC)—N(3L) | 153(4) |
| O(10W)—N(1L)—C(1LA)—N(3L) | −103(3) | C(2LB)—N(1L)—C(1LC)—N(3L) | 65(4) |
| C(2L)—N(1L)—C(1LA)—N(3L) | 176(4) | C(1LA)—N(1L)—C(1LC)—N(3L) | 4(3) |
| N(3L)—N(1L)—C(1LA)—C(5LD) | 175(3) | O(10W)—N(1L)—C(1LC)—N(3L) | −85(4) |
| N(2L)—N(1L)—C(1LA)—C(5LD) | −53(5) | C(2L)—N(1L)—C(1LC)—N(3L) | 14(6) |
| C(2LB)—N(1L)—C(1LA)—C(5LD) | −60(2) | N(3L)—N(1L)—C(1LC)—C(5LD) | −4(4) |
| C(1LC)—N(1L)—C(1LA)—C(5LD) | 0(3) | N(2L)—N(1L)—C(1LC)—C(5LD) | 150(3) |
| O(10W)—N(1L)—C(1LA)—C(5LD) | 73(2) | C(2LB)—N(1L)—C(1LC)—C(5LD) | 61(2) |
| C(2L)—N(1L)—C(1LA)—C(5LD) | −8(3) | C(1LA)—N(1L)—C(1LC)—C(5LD) | 0(2) |
| N(3L)—N(1L)—C(1LA)—C(3LD) | 127(4) | O(10W)—N(1L)—C(1LC)—C(5LD) | −88(2) |
| N(2L)—N(1L)—C(1LA)—C(3LD) | −102(5) | C(2L)—N(1L)—C(1LC)—C(5LD) | 11(3) |
| C(2LB)—N(1L)—C(1LA)—C(3LD) | −108(3) | N(3L)—N(1L)—C(2LB)—C(1LC) | 137(3) |
| C(1LC)—N(1L)—C(1LA)—C(3LD) | −49(3) | N(2L)—N(1L)—C(2LB)—C(1LC) | −70(3) |
| O(10W)—N(1L)—C(1LA)—C(3LD) | 24(3) | C(1LA)—N(1L)—C(2LB)—C(1LC) | 106(2) |
| C(2L)—N(1L)—C(1LA)—C(3LD) | −57(3) | O(10W)—N(1L)—C(2LB)—C(1LC) | 38(3) |

TABLE 3-continued

Torsion angles [°] (cf. FIG. 4)

| | | | |
|---|---|---|---|
| N(3L)—N(1L)—C(1LA)—C(2LB) | −125(3) | C(2L)—N(1L)—C(2LB)—C(1LC) | 43(3) |
| N(2L)—N(1L)—C(1LA)—C(2LB) | 6(5) | N(3L)—N(1L)—C(2LB)—C(2L) | 94(4) |
| C(1LC)—N(1L)—C(1LA)—C(2LB) | 60(2) | N(2L)—N(1L)—C(2LB)—C(2L) | −113(4) |
| O(10W)—N(1L)—C(1LA)—C(2LB) | 132(2) | C(1LC)—N(1L)—C(2LB)—C(2L) | −43(3) |
| C(2L)—N(1L)—C(1LA)—C(2LB) | 51(2) | C(1LA)—N(1L)—C(2LB)—C(2L) | 63(3) |
| N(3L)—N(1L)—C(1LA)—C(2LD) | −121(3) | O(10W)—N(1L)—C(2LB)—C(2L) | −5(4) |
| N(2L)—N(1L)—C(1LA)—C(2LD) | 10(5) | N(3L)—N(1L)—C(2LB)—N(2L) | −153(3) |
| C(2LB)—N(1L)—C(1LA)—C(2LD) | 4(2) | C(1LC)—N(1L)—C(2LB)—N(2L) | 70(3) |
| C(1LC)—N(1L)—C(1LA)—C(2LD) | 64(3) | C(1LA)—N(1L)—C(2LB)—N(2L) | 176(3) |
| O(10W)—N(1L)—C(1LA)—C(2LD) | 136(2) | O(10W)—N(1L)—C(2LB)—N(2L) | 108(4) |
| C(2L)—N(1L)—C(1LA)—C(2LD) | 55(3) | C(2L)—N(1L)—C(2LB)—N(2L) | 113(4) |
| N(3L)—N(1L)—C(1LA)—C(2L) | −176(4) | N(2L)—N(1L)—C(2LB)—N(3L) | 153(3) |
| N(2L)—N(1L)—C(1LA)—C(2L) | −45(5) | C(1LC)—N(1L)—C(2LB)—N(3L) | −137(3) |
| C(2LB)—N(1L)—C(1LA)—C(2L) | −51(2) | C(1LA)—N(1L)—C(2LB)—N(3L) | −30.7(19) |
| C(1LC)—N(1L)—C(1LA)—C(2L) | 8(3) | O(10W)—N(1L)—C(2LB)—N(3L) | −99(3) |
| O(10W)—N(1L)—C(1LA)—C(2L) | 81(2) | C(2L)—N(1L)—C(2LB)—N(3L) | −94(4) |
| N(3L)—N(1L)—C(1LC)—C(2L) | −14(6) | N(3L)—N(1L)—C(2LB)—C(2LC) | 42(3) |
| N(2L)—N(1L)—C(1LC)—C(2L) | 139(5) | N(2L)—N(1L)—C(2LB)—C(2LC) | −165(3) |
| C(2LB)—N(1L)—C(1LC)—C(2L) | 50(4) | C(1LC)—N(1L)—C(2LB)—C(2LC) | −95(3) |
| C(1LA)—N(1L)—C(1LC)—C(2L) | −11(4) | C(1LA)—N(1L)—C(2LB)—C(2LC) | 11.1(18) |
| O(10W)—N(1L)—C(1LC)—C(2L) | −99(4) | O(10W)—N(1L)—C(2LB)—C(2LC) | −57(3) |
| N(3L)—N(1L)—C(1LC)—N(2L) | −153(4) | C(2L)—N(1L)—C(2LB)—C(2LC) | −52(3) |
| N(3L)—N(1L)—C(2LB)—C(1LA) | 30.7(19) | N(2L)—C(1LC)—C(2LB)—C(1LA) | 180(4) |
| N(2L)—N(1L)—C(2LB)—C(1LA) | −176(3) | O(10W)—C(1LC)—C(2LB)—C(2LD) | 93(4) |
| C(1LC)—N(1L)—C(2LB)—C(1LA) | −106(2) | N(3L)—C(1LC)—C(2LB)—C(2LD) | 101(3) |
| O(10W)—N(1L)—C(2LB)—C(1LA) | −68(3) | C(5LD)—C(1LC)—C(2LB)—C(2LD) | 11(3) |
| C(2L)—N(1L)—C(2LB)—C(1LA) | −63(3) | N(1L)—C(1LC)—C(2LB)—C(5LD) | 114(2) |
| N(3L)—N(1L)—C(2LB)—C(2LD) | 25(4) | C(2L)—C(1LC)—C(2LB)—C(5LD) | −12(3) |
| N(2L)—N(1L)—C(2LB)—C(2LD) | 178(4) | N(2L)—C(1LC)—C(2LB)—C(5LD) | 168(3) |
| C(1LC)—N(1L)—C(2LB)—C(2LD) | −111(4) | O(10W)—C(1LC)—C(2LB)—C(5LD) | 81(3) |
| C(1LA)—N(1L)—C(2LB)—C(2LD) | −5(3) | N(3L)—C(1LC)—C(2LB)—C(5LD) | 89.7(19) |
| O(10W)—N(1L)—C(2LB)—C(2LD) | −74(5) | C(2LC)—C(1LA)—C(2LB)—N(1L) | 159(3) |
| C(2L)—N(1L)—C(2LB)—C(2LD) | −69(4) | N(3L)—C(1LA)—C(2LB)—N(1L) | −25.3(16) |
| N(3L)—N(1L)—C(2LB)—C(5LD) | 75(3) | C(5LD)—C(1LA)—C(2LB)—N(1L) | 116(2) |
| N(2L)—N(1L)—C(2LB)—C(5LD) | −131(3) | C(3LD)—C(1LA)—C(2LB)—N(1L) | 94(3) |
| C(1LC)—N(1L)—C(2LB)—C(5LD) | −61(3) | C(2LD)—C(1LA)—C(2LB)—N(1L) | −176(3) |
| C(1LA)—N(1L)—C(2LB)—C(5LD) | 44.8(18) | C(2L)—C(1LA)—C(2LB)—N(1L) | 105(3) |
| O(10W)—N(1L)—C(2LB)—C(5LD) | −23(3) | C(2LC)—C(1LA)—C(2LB)—C(1LC) | 102(4) |
| C(2L)—N(1L)—C(2LB)—C(5LD) | −19(3) | N(3L)—C(1LA)—C(2LB)—C(1LC) | −82(3) |
| C(2L)—C(1LC)—C(2LB)—N(1L) | −126(4) | C(5LD)—C(1LA)—C(2LB)—C(1LC) | 60(3) |
| N(2L)—C(1LC)—C(2LB)—N(1L) | 55(2) | C(3LD)—C(1LA)—C(2LB)—C(1LC) | 37(4) |
| O(10W)—C(1LC)—C(2LB)—N(1L) | −32(3) | C(2LD)—C(1LA)—C(2LB)—C(1LC) | 128(3) |
| N(3L)—C(1LC)—C(2LB)—N(1L) | −24.1(17) | C(2L)—C(1LA)—C(2LB)—C(1LC) | 49(3) |
| C(5LD)—C(1LC)—C(2LB)—N(1L) | −114(2) | N(1L)—C(1LA)—C(2LB)—C(1LC) | −57(2) |
| N(1L)—C(1LC)—C(2LB)—C(2L) | 126(4) | C(2LC)—C(1LA)—C(2LB)—C(2L) | 53(4) |
| N(2L)—C(1LC)—C(2LB)—C(2L) | −180(4) | N(3L)—C(1LA)—C(2LB)—C(2L) | −131(3) |
| O(10W)—C(1LC)—C(2LB)—C(2L) | 93(4) | C(5LD)—C(1LA)—C(2LB)—C(2L) | 11(3) |
| N(3L)—C(1LC)—C(2LB)—C(2L) | 102(4) | C(3LD)—C(1LA)—C(2LB)—C(2L) | −11(4) |
| C(5LD)—C(1LC)—C(2LB)—C(2L) | 12(3) | C(2LD)—C(1LA)—C(2LB)—C(2L) | 79(3) |
| N(1L)—C(1LC)—C(2LB)—N(2L) | −55(2) | N(1L)—C(1LA)—C(2LB)—C(2L) | −105(3) |
| C(2L)—C(1LC)—C(2LB)—N(2L) | 180(4) | C(2LC)—C(1LA)—C(2LB)—N(2L) | 156(4) |
| O(10W)—C(1LC)—C(2LB)—N(2L) | −87(3) | N(3L)—C(1LA)—C(2LB)—N(2L) | −29(3) |
| N(3L)—C(1LC)—C(2LB)—N(2L) | −79(3) | C(5LD)—C(1LA)—C(2LB)—N(2L) | 113(3) |
| C(5LD)—C(1LC)—C(2LB)—N(2L) | −168(3) | C(3LD)—C(1LA)—C(2LB)—N(2L) | 91(4) |
| N(1L)—C(1LC)—C(2LB)—N(3L) | 24.1(17) | C(2LD)—C(1LA)—C(2LB)—N(2L) | −179(3) |
| C(2L)—C(1LC)—C(2LB)—N(3L) | −102(4) | C(2L)—C(1LA)—C(2LB)—N(2L) | 102(4) |
| N(2L)—C(1LC)—C(2LB)—N(3L) | 79(3) | N(1L)—C(1LA)—C(2LB)—N(2L) | −3(2) |
| O(10W)—C(1LC)—C(2LB)—N(3L) | −8(3) | C(2LC)—C(1LA)—C(2LB)—N(3L) | −176(4) |
| C(5LD)—C(1LC)—C(2LB)—N(3L) | −89.7(19) | C(5LD)—C(1LA)—C(2LB)—N(3L) | 141(2) |
| N(1L)—C(1LC)—C(2LB)—C(2LC) | 100(3) | C(3LD)—C(1LA)—C(2LB)—N(3L) | 119(3) |
| C(2L)—C(1LC)—C(2LB)—C(2LC) | −26(4) | C(2LD)—C(1LA)—C(2LB)—N(3L) | −150(3) |
| N(2L)—C(1LC)—C(2LB)—C(2LC) | 154(3) | C(2L)—C(1LA)—C(2LB)—N(3L) | 131(3) |
| O(10W)—C(1LC)—C(2LB)—C(2LC) | 67(3) | N(1L)—C(1LA)—C(2LB)—N(3L) | 25.3(16) |
| N(3L)—C(1LC)—C(2LB)—C(2LC) | 76(2) | N(3L)—C(1LA)—C(2LB)—C(2LC) | 176(4) |
| C(5LD)—C(1LC)—C(2LB)—C(2LC) | −14(2) | C(5LD)—C(1LA)—C(2LB)—C(2LC) | −43(3) |
| N(1L)—C(1LC)—C(2LB)—C(1LA) | 69(2) | C(3LD)—C(1LA)—C(2LB)—C(2LC) | −65(4) |
| C(2L)—C(1LC)—C(2LB)—C(1LA) | −57(3) | C(2LD)—C(1LA)—C(2LB)—C(2LC) | 26(3) |
| N(2L)—C(1LC)—C(2LB)—C(1LA) | 123(3) | C(2L)—C(1LA)—C(2LB)—C(2LC) | −53(4) |
| O(10W)—C(1LC)—C(2LB)—C(1LA) | 36(3) | N(1L)—C(1LA)—C(2LB)—C(2LC) | −159(3) |
| N(3L)—C(1LC)—C(2LB)—C(1LA) | 44.8(13) | C(2LC)—C(1LA)—C(2LB)—C(2LD) | −26(3) |
| C(5LD)—C(1LC)—C(2LB)—C(1LA) | −45(2) | N(3L)—C(1LA)—C(2LB)—C(2LD) | 150(3) |
| N(1L)—C(1LC)—C(2LB)—C(2LD) | 125(4) | C(5LD)—C(1LA)—C(2LB)—C(2LD) | −68(3) |
| C(2L)—C(1LA)—C(2LB)—C(2LD) | −1(5) | C(3LD)—C(1LA)—C(2LB)—C(2LD) | −90(4) |
| C(2L)—C(1LA)—C(2LB)—C(2LD) | −79(3) | C(2LC)—C(2LB)—C(2L)—C(5LD) | 5(8) |
| N(1L)—C(1LA)—C(2LB)—C(2LD) | 176(3) | C(1LA)—C(2LB)—C(2L)—C(5LD) | −27(8) |
| C(2LC)—C(1LA)—C(2LB)—C(5LD) | 43(3) | C(2LD)—C(2LB)—C(2L)—C(5LD) | 37(9) |
| N(3L)—C(1LA)—C(2LB)—C(5LD) | −141(2) | N(1L)—C(2LB)—C(2L)—C(1LC) | 45(3) |
| C(3LD)—C(1LA)—C(2LB)—C(5LD) | −22(3) | N(2L)—C(2LB)—C(2L)—C(1LC) | 0(4) |

TABLE 3-continued

Torsion angles [°] (cf. FIG. 4)

| | | |
|---|---|---|
| C(2LD)—C(1LA)—C(2LB)—C(5LD) | 68(3) | |
| C(2L)—C(1LA)—C(2LB)—C(5LD) | −11(3) | |
| N(1L)—C(1LA)—C(2LB)—C(5LD) | −116(2) | |
| N(1L)—C(1LC)—C(2L)—C(5LD) | 64(16) | |
| N(2L)—C(1LC)—C(2L)—C(5LD) | 109(15) | |
| C(2LB)—C(1LC)—C(2L)—C(5LD) | 109(16) | |
| O(10W)—C(1LC)—C(2L)—C(5LD) | −6(16) | |
| N(3L)—C(1LC)—C(2L)—C(5LD) | 59(15) | |
| N(1L)—C(1LC)—C(2L)—C(2LC) | −7(7) | |
| N(2L)—C(1LC)—C(2L)—C(2LC) | 37(9) | |
| C(2LB)—C(1LC)—C(2L)—C(2LC) | 37(5) | |
| O(10W)—C(1LC)—C(2L)—C(2LC) | −78(6) | |
| N(3L)—C(1LC)—C(2L)—C(2LC) | −12(5) | |
| C(5LD)—C(1LC)—C(2L)—C(2LC) | −72(15) | |
| N(1L)—C(1LC)—C(2L)—C(2LB) | −44(3) | |
| N(2L)—C(1LC)—C(2L)—C(2LB) | 0(6) | |
| O(10W)—C(1LC)—C(2L)—C(2LB) | −115(3) | |
| N(3L)—C(1LC)—C(2L)—C(2LB) | −49.1(19) | |
| C(5LD)—C(1LC)—C(2L)—C(2LB) | −109(16) | |
| N(1L)—C(1LC)—C(2L)—C(1LA) | 11(4) | |
| N(2L)—C(1LC)—C(2L)—C(1LA) | 56(7) | |
| C(2LB)—C(1LC)—C(2L)—C(1LA) | 55(3) | |
| O(10W)—C(1LC)—C(2L)—C(1LA) | −60(3) | |
| N(3L)—C(1LC)—C(2L)—C(1LA) | 6(2) | |
| C(5LD)—C(1LC)—C(2L)—C(1LA) | −53(14) | |
| N(1L)—C(1LC)—C(2L)—C(2LD) | −44(6) | |
| N(2L)—C(1LC)—C(2L)—C(2LD) | 1(9) | |
| C(2LB)—C(1LC)—C(2L)—C(2LD) | 1(4) | |
| O(10W)—C(1LC)—C(2L)—C(2LD) | −114(5) | |
| N(3L)—C(1LC)—C(2L)—C(2LD) | −49(5) | |
| C(5LD)—C(1LC)—C(2L)—C(2LD) | −108(17) | |
| N(2L)—C(1LC)—C(2L)—N(1L) | 45(5) | |
| C(2LB)—C(1LC)—C(2L)—N(1L) | 44(3) | |
| O(10W)—C(1LC)—C(2L)—N(1L) | −71(3) | |
| N(3L)—C(1LC)—C(2L)—N(1L) | −5.0(19) | |
| C(5LD)—C(1LC)—C(2L)—N(1L) | −64(16) | |
| N(1L)—C(1LC)—C(2L)—C(3LD) | 61(5) | |
| N(2L)—C(1LC)—C(2L)—C(3LD) | 106(6) | |
| C(2LB)—C(1LC)—C(2L)—C(3LD) | 105(4) | |
| O(10W)—C(1LC)—C(2L)—C(3LD) | −10(5) | |
| N(3L)—C(1LC)—C(2L)—C(3LD) | 56(4) | |
| C(5LD)—C(1LC)—C(2L)—C(3LD) | −3(12) | |
| N(1L)—C(2LB)—C(2L)—C(5LD) | −97(9) | |
| C(1LC)—C(2LB)—C(2L)—C(5LD) | −142(10) | |
| N(2L)—C(2LB)—C(2L)—C(5LD) | −142(9) | |
| N(3L)—C(2LB)—C(2L)—C(5LD) | −60(9) | |
| N(1L)—C(1LA)—C(2L)—C(5LD) | −161(6) | |
| C(2LC)—C(1LA)—C(2L)—C(1LC) | −147(6) | |
| N(3L)—C(1LA)—C(2L)—C(1LC) | −10(4) | |
| C(5LD)—C(1LA)—C(2L)—C(1LC) | 153(8) | |
| C(3LD)—C(1LA)—C(2L)—C(1LC) | 120(4) | |
| C(2LB)—C(1LA)—C(2L)—C(1LC) | −50(3) | |
| C(2LD)—C(1LA)—C(2L)—C(1LC) | −124(4) | |
| N(1L)—C(1LA)—C(2L)—C(1LC) | −8(3) | |
| N(3L)—C(1LA)—C(2L)—C(2LC) | 137(4) | |
| C(5LD)—C(1LA)—C(2L)—C(2LC) | −60(6) | |
| C(3LD)—C(1LA)—C(2L)—C(2LC) | −93(5) | |
| C(2LB)—C(1LA)—C(2L)—C(2LC) | 97(4) | |
| C(2LD)—C(1LA)—C(2L)—C(2LC) | 23(4) | |
| N(1L)—C(1LA)—C(2L)—C(2LC) | 139(4) | |
| C(2LC)—C(1LA)—C(2L)—C(2LB) | −97(4) | |
| N(3L)—C(1LA)—C(2L)—C(2LB) | 40(3) | |
| C(5LD)—C(1LA)—C(2L)—C(2LB) | −157(7) | |
| C(3LD)—C(1LA)—C(2L)—C(2LB) | 170(4) | |
| C(2LD)—C(1LA)—C(2L)—C(2LB) | −74(3) | |
| N(1L)—C(1LA)—C(2L)—C(2LB) | 42(2) | |
| C(2LC)—C(1LA)—C(2L)—C(2LD) | −23(4) | |
| N(3L)—C(1LA)—C(2L)—C(2LD) | 115(3) | |
| C(5LD)—C(1LA)—C(2L)—C(2LD) | −82(6) | |
| C(3LD)—C(1LA)—C(2L)—C(2LD) | −116(3) | |
| C(2LB)—C(1LA)—C(2L)—C(2LD) | 74(3) | |
| N(1L)—C(1LA)—C(2L)—C(2LD) | 116(3) | |
| C(2LC)—C(1LA)—C(2L)—N(1L) | −139(4) | |
| N(3L)—C(1LA)—C(2L)—N(1L) | −1.6(16) | |
| C(5LD)—C(1LA)—C(2L)—N(1L) | 161(6) | |
| C(3LD)—C(1LA)—C(2L)—N(1L) | 128(2) | |
| C(2LB)—C(1LA)—C(2L)—N(1L) | −42(2) | |
| C(2LD)—C(1LA)—C(2L)—N(1L) | −116(3) | |
| N(3L)—C(2LB)—C(2L)—C(1LC) | 82(3) | |
| C(2LA)—C(2LB)—C(2L)—C(1LC) | 147(4) | |
| C(1LA)—C(2LB)—C(2L)—C(1LC) | 115(3) | |
| C(2LD)—C(2LB)—C(2L)—C(1LC) | 180(4) | |
| C(5LD)—C(2LB)—C(2L)—C(1LC) | 142(11) | |
| N(1L)—C(2LB)—C(2L)—C(2LC) | −102(3) | |
| C(1LC)—C(2LB)—C(2L)—C(2LC) | −147(4) | |
| N(2L)—C(2LB)—C(2L)—C(2LC) | −147(3) | |
| N(3L)—C(2LB)—C(2L)—C(2LC) | −65(3) | |
| C(1LA)—C(2LB)—C(2L)—C(2LC) | −32(2) | |
| C(2LD)—C(2LB)—C(2L)—C(2LC) | 33(3) | |
| C(5LD)—C(2LB)—C(2L)—C(2LC) | −5(8) | |
| N(1L)—C(2LB)—C(2L)—C(1LA) | −70(2) | |
| C(1LC)—C(2LB)—C(2L)—C(1LA) | −115(3) | |
| N(2L)—C(2LB)—C(2L)—C(1LA) | −115(3) | |
| N(3L)—C(2LB)—C(2L)—C(1LA) | −33(2) | |
| C(2LC)—C(2LB)—C(2L)—C(1LA) | 32(2) | |
| C(2LD)—C(2LB)—C(2L)—C(1LA) | 65(2) | |
| C(5LD)—C(2LB)—C(2L)—C(1LA) | 27(8) | |
| N(1L)—C(2LB)—C(2L)—C(2LD) | −134(3) | |
| C(1LC)—C(2LB)—C(2L)—C(2LD) | −180(4) | |
| N(2L)—C(2LB)—C(2L)—C(2LD) | −180(3) | |
| N(3L)—C(2LB)—C(2L)—C(2LD) | −98(2) | |
| C(2LC)—C(2LB)—C(2L)—C(2LD) | −33(3) | |
| C(1LA)—C(2LB)—C(2L)—C(2LD) | −65(2) | |
| C(5LD)—C(2LB)—C(2L)—C(2LD) | −37(9) | |
| C(1LC)—C(2LB)—C(2L)—N(1L) | −45(3) | |
| N(2L)—C(2LB)—C(2L)—N(1L) | −45(2) | |
| N(3L)—C(2LB)—C(2L)—N(1L) | 36.9(14) | |
| C(2LC)—C(2LB)—C(2L)—N(1L) | 102(3) | |
| C(1LA)—C(2LB)—C(2L)—N(1L) | 70(2) | |
| C(2LD)—C(2LB)—C(2L)—N(1L) | 134(3) | |
| C(5LD)—C(2LB)—C(2L)—N(1L) | 97(9) | |
| N(1L)—C(2LB)—C(2L)—C(3LD) | −61(5) | |
| C(1LC)—C(2LB)—C(2L)—C(3LD) | −106(5) | |
| N(2L)—C(2LB)—C(2L)—C(3LD) | −106(4) | |
| N(3L)—C(2LB)—C(2L)—C(3LD) | −24(5) | |
| C(2LC)—C(2LB)—C(2L)—C(3LD) | 41(3) | |
| C(1LA)—C(2LB)—C(2L)—C(3LD) | 9(3) | |
| C(2LD)—C(2LB)—C(2L)—C(3LD) | 73(4) | |
| C(5LD)—C(2LB)—C(2L)—C(3LD) | 36(7) | |
| C(2LC)—C(1LA)—C(2L)—C(5LD) | 60(6) | |
| N(3L)—C(1LA)—C(2L)—C(5LD) | −163(6) | |
| C(3LD)—C(1LA)—C(2L)—C(5LD) | −33(5) | |
| C(2LB)—C(1LA)—C(2L)—C(5LD) | 157(7) | |
| C(2LD)—C(1LA)—C(2L)—C(5LD) | 82(6) | |
| C(2LB)—N(1L)—C(2L)—C(2LC) | 70(3) | |
| C(1LC)—N(1L)—C(2L)—C(2LC) | 174(6) | |
| C(1LA)—N(1L)—C(2L)—C(2LC) | −20(2) | |
| O(10W)—N(1L)—C(2L)—C(2LC) | −114(3) | |
| N(3L)—N(1L)—C(2L)—C(2LB) | −87(3) | |
| N(2L)—N(1L)—C(2L)—C(2LB) | 66(4) | |
| C(1LC)—N(1L)—C(2L)—C(2LB) | 104(5) | |
| C(1LA)—N(1L)—C(2L)—C(2LB) | −89(3) | |
| O(10W)—N(1L)—C(2L)—C(2LB) | 176(4) | |
| N(3L)—N(1L)—C(2L)—C(1LA) | 2(2) | |
| N(2L)—N(1L)—C(2L)—C(1LA) | 155(3) | |
| C(2LB)—N(1L)—C(2L)—C(1LA) | 89(3) | |
| C(1LC)—N(1L)—C(2L)—C(1LA) | −167(5) | |
| O(10W)—N(1L)—C(2L)—C(1LA) | −95(2) | |
| N(3L)—N(1L)—C(2L)—C(2LD) | −47(2) | |
| N(2L)—N(1L)—C(2L)—C(2LD) | 106(4) | |
| C(2LB)—N(1L)—C(2L)—C(2LD) | 40(3) | |
| C(1LC)—N(1L)—C(2L)—C(2LD) | 144(5) | |
| C(1LA)—N(1L)—C(2L)—C(2LD) | −49(2) | |
| O(10W)—N(1L)—C(2L)—C(2LD) | −144(3) | |
| N(3L)—N(1L)—C(2L)—C(3LD) | 41(3) | |
| N(2L)—N(1L)—C(2L)—C(3LD) | −166(3) | |
| C(2LB)—N(1L)—C(2L)—C(3LD) | 128(4) | |
| C(1LC)—N(1L)—C(2L)—C(3LD) | −128(5) | |
| C(1LA)—N(1L)—C(2L)—C(3LD) | 39(2) | |
| O(10W)—N(1L)—C(2L)—C(3LD) | −56(3) | |
| N(3L)—N(1L)—N(2L)—C(1LC) | 135(7) | |
| C(2LB)—N(1L)—N(2L)—C(1LC) | 66(3) | |
| C(1LA)—N(1L)—N(2L)—C(1LC) | 60(5) | |
| O(10W)—N(1L)—N(2L)—C(1LC) | −60(3) | |
| C(2L)—N(1L)—N(2L)—C(1LC) | 24(3) | |
| N(3L)—N(1L)—N(2L)—C(2LB) | 69(7) | |

TABLE 3-continued

Torsion angles [°] (cf. FIG. 4)

| | | | | |
|---|---|---|---|---|
| C(2LC)—C(1LA)—C(2L)—C(3LD) | 93(5) | C(1LC)—N(1L)—N(2L)—C(2LB) | −66(2) |
| N(3L)—C(1LA)—C(2L)—C(3LD) | −130(3) | C(1LA)—N(1L)—N(2L)—C(2LB) | −6(4) |
| C(5LD)—C(1LA)—C(2L)—C(3LD) | 33(6) | O(10W)—N(1L)—N(2L)—C(2LB) | −126(3) |
| C(2LB)—C(1LA)—C(2L)—C(3LD) | −170(4) | C(2L)—N(1L)—N(2L)—C(2LB) | −41(2) |
| C(2LD)—C(1LA)—C(2L)—C(3LD) | 116(3) | C(2LB)—N(1L)—N(2L)—N(3L) | −69(7) |
| N(1L)—C(1LA)—C(2L)—C(3LD) | −128(2) | C(1LC)—N(1L)—N(2L)—N(3L) | −135(7) |
| N(3L)—N(1L)—C(2L)—C(5LD) | 23(8) | C(1LA)—N(1L)—N(2L)—N(3L) | −75(7) |
| N(2L)—N(1L)—C(2L)—C(5LD) | 176(8) | O(10W)—N(1L)—N(2L)—N(3L) | 165(8) |
| C(2LB)—N(1L)—C(2L)—C(5LD) | 110(9) | C(2L)—N(1L)—N(2L)—N(3L) | −111(7) |
| C(1LC)—N(1L)—C(2L)—C(5LD) | −146(10) | N(3L)—N(1L)—N(2L)—C(4LD) | 151(6) |
| C(1LA)—N(1L)—C(2L)—C(5LD) | 20(7) | C(2LB)—N(1L)—N(2L)—C(4LD) | 82(7) |
| O(10W)—N(1L)—C(2L)—C(5LD) | −74(8) | C(1LC)—N(1L)—N(2L)—C(4LD) | 16(6) |
| N(3L)—N(1L)—C(2L)—C(1LC) | 169(4) | C(1LA)—N(1L)—N(2L)—C(4LD) | 76(8) |
| N(2L)—N(1L)—C(2L)—C(1LC) | −38(4) | O(10W)—N(1L)—N(2L)—C(4LD) | −44(7) |
| C(2LB)—N(1L)—C(2L)—C(1LC) | −104(5) | C(2L)—N(1L)—N(2L)—C(4LD) | 41(7) |
| C(1LA)—N(1L)—C(2L)—C(1LC) | 167(5) | C(2L)—C(1LC)—N(2L)—N(1L) | −65(6) |
| O(10W)—N(1L)—C(2L)—C(1LC) | 72(4) | C(2LB)—C(1LC)—N(2L)—N(1L) | −64(2) |
| N(3L)—N(1L)—C(2L)—C(2LC) | −17(3) | O(10W)—C(1LC)—N(2L)—N(1L) | 53(3) |
| N(2L)—N(1L)—C(2L)—C(2LC) | 136(4) | N(3L)—C(1LC)—N(2L)—N(1L) | −9.7(17) |
| C(5LD)—C(1LC)—N(2L)—N(1L) | −48(5) | N(1L)—C(1LA)—C(2LC)—C(2LD) | 83(7) |
| N(1L)—C(1LC)—N(2L)—C(2LB) | 64(2) | N(3L)—C(1LA)—C(2LC)—C(5LD) | −94(5) |
| C(2L)—C(1LC)—N(2L)—C(2LB) | 0(6) | C(3LD)—C(1LA)—C(2LC)—C(5LD) | 38(4) |
| O(10W)—C(1LC)—N(2L)—C(2LB) | 117(3) | C(2LB)—C(1LA)—C(2LC)—C(5LD) | −90(4) |
| N(3L)—C(1LC)—N(2L)—C(2LB) | 54.5(18) | C(2LD)—C(1LA)—C(2LC)—C(5LD) | −159(9) |
| C(5LD)—C(1LC)—N(2L)—C(2LB) | 16(4) | C(2L)—C(1LA)—C(2LC)—C(5LD) | −37(4) |
| N(1L)—C(1LC)—N(2L)—N(3L) | 9.7(17) | N(1L)—C(1LA)—C(2LC)—C(5LD) | −76(4) |
| C(2L)—C(1LC)—N(2L)—N(3L) | −55(6) | N(3L)—C(1LA)—C(2LC)—C(2L) | −57(5) |
| C(2LB)—C(1LC)—N(2L)—N(3L) | −54.5(18) | C(5LD)—C(1LA)—C(2LC)—C(2L) | 37(4) |
| O(10W)—C(1LC)—N(2L)—N(3L) | 62.5(19) | C(3LD)—C(1LA)—C(2LC)—C(2L) | 75(4) |
| C(5LD)—C(1LC)—N(2L)—N(3L) | −38(4) | C(2LB)—C(1LA)—C(2LC)—C(2L) | −53(3) |
| N(1L)—C(1LC)—N(2L)—C(4LD) | −171(3) | C(2LD)—C(1LA)—C(2LC)—C(2L) | −122(8) |
| C(2L)—C(1LC)—N(2L)—C(4LD) | 124(6) | N(1L)—C(1LA)—C(2LC)—C(2L) | −39(4) |
| C(2LB)—C(1LC)—N(2L)—C(4LD) | 124(3) | N(3L)—C(1LA)—C(2LC)—C(2LB) | −4(4) |
| O(10W)—C(1LC)—N(2L)—C(4LD) | −119(3) | C(5LD)—C(1LA)—C(2LC)—C(2LB) | 90(4) |
| N(3L)—C(1LC)—N(2L)—C(4LD) | 179(2) | C(3LD)—C(1LA)—C(2LC)—C(2LB) | 128(2) |
| C(5LD)—C(1LC)—N(2L)—C(4LD) | 141(4) | C(2LD)—C(1LA)—C(2LC)—C(2LB) | −69(7) |
| C(1LC)—C(2LB)—N(2L)—N(1L) | 79(3) | C(2L)—C(1LA)—C(2LC)—C(2LB) | 53(3) |
| C(2L)—C(2LB)—N(2L)—N(1L) | 79(4) | N(1L)—C(1LA)—C(2LC)—C(2LB) | 14(2) |
| N(3L)—C(2LB)—N(2L)—N(1L) | −16(2) | N(3L)—C(1LA)—C(2LC)—C(3LD) | −133(4) |
| C(2LC)—C(2LB)—N(2L)—N(1L) | 27(6) | C(5LD)—C(1LA)—C(2LC)—C(3LD) | −38(4) |
| C(1LA)—C(2LB)—N(2L)—N(1L) | 4(3) | C(2LB)—C(1LA)—C(2LC)—C(3LD) | −128(2) |
| C(2LD)—C(2LB)—N(2L)—N(1L) | −90(100) | C(2LD)—C(1LA)—C(2LC)—C(3LD) | 163(7) |
| C(5LD)—C(2LB)—N(2L)—N(1L) | 66(4) | C(2L)—C(1LA)—C(2LC)—C(3LD) | −75(4) |
| N(1L)—C(2LB)—N(2L)—C(1LC) | −79(3) | N(1L)—C(1LA)—C(2LC)—C(3LD) | −114(3) |
| C(2L)—C(2LB)—N(2L)—C(1LC) | 0(4) | C(5LD)—C(1LA)—C(2LC)—N(3L) | 94(5) |
| N(3L)—C(2LB)—N(2L)—C(1LC) | −95(3) | C(3LD)—C(1LA)—C(2LC)—N(3L) | 133(4) |
| C(2LC)—C(2LB)—N(2L)—C(1LC) | −52(5) | C(2LB)—C(1LA)—C(2LC)—N(3L) | 4(4) |
| C(1LA)—C(2LB)—N(2L)—C(1LC) | −75(3) | C(2LD)—C(1LA)—C(2LC)—N(3L) | −64(8) |
| C(2LD)—C(2LB)—N(2L)—C(1LC) | −169(100) | C(2L)—C(1LA)—C(2LC)—N(3L) | 57(5) |
| C(5LD)—C(2LB)—N(2L)—C(1LC) | −13(4) | N(1L)—C(1LA)—C(2LC)—N(3L) | 18(2) |
| N(1L)—C(2LB)—N(2L)—N(3L) | 16(2) | C(5LD)—C(2L)—C(2LC)—C(1LA) | −105(7) |
| C(1LC)—C(2LB)—N(2L)—N(3L) | 95(3) | C(1LC)—C(2L)—C(2LC)—C(1LA) | 39(7) |
| C(2L)—C(2LB)—N(2L)—N(3L) | 95(3) | C(2LB)—C(2L)—C(2LC)—C(1LA) | 71(4) |
| C(2LC)—C(2LB)—N(2L)—N(3L) | 43(5) | C(2LD)—C(2L)—C(2LC)—C(1LA) | 141(6) |
| C(1LA)—C(2LB)—N(2L)—N(3L) | 20.2(19) | N(1L)—C(2L)—C(2LC)—C(1LA) | 34(4) |
| C(2LD)—C(2LB)—N(2L)—N(3L) | −74(100) | C(3LD)—C(2L)—C(2LC)—C(1LA) | −66(4) |
| C(5LD)—C(2LB)—N(2L)—N(3L) | 81(3) | C(5LD)—C(2L)—C(2LC)—C(2LD) | 115(7) |
| N(1L)—C(2LB)—N(2L)—C(4LD) | −144(4) | C(1LC)—C(2L)—C(2LC)—C(2LD) | −102(6) |
| C(1LC)—C(2LB)—N(2L)—C(4LD) | −65(3) | C(2LB)—C(2L)—C(2LC)—C(2LD) | −70(5) |
| C(2L)—C(2LB)—N(2L)—C(4LD) | −65(5) | C(1LA)—C(2L)—C(2LC)—C(2LD) | −141(6) |
| N(3L)—C(2LB)—N(2L)—C(4LD) | −160(3) | N(1L)—C(2L)—C(2LC)—C(2LD) | −107(4) |
| C(2LC)—C(2LB)—N(2L)—C(4LD) | −117(5) | C(3LD)—C(2L)—C(2LC)—C(2LD) | 153(5) |
| C(1LA)—C(2LB)—N(2L)—C(4LD) | −140(3) | C(1LC)—C(2L)—C(2LC)—C(5LD) | 143(10) |
| C(2LD)—C(2LB)—N(2L)—C(4LD) | 126(100) | C(2LB)—C(2L)—C(2LC)—C(5LD) | 176(7) |
| C(5LD)—C(2LB)—N(2L)—C(4LD) | −79(4) | C(1LA)—C(2L)—C(2LC)—C(5LD) | 105(7) |
| N(3L)—C(1LA)—C(2LC)—C(2LD) | 64(8) | C(2LD)—C(2L)—C(2LC)—C(5LD) | −115(7) |
| C(5LD)—C(1LA)—C(2LC)—C(2LD) | 159(9) | N(1L)—C(2L)—C(2LC)—C(5LD) | 139(7) |
| C(3LD)—C(1LA)—C(2LC)—C(2LD) | −163(7) | C(3LD)—C(2L)—C(2LC)—C(5LD) | 38(6) |
| C(2LB)—C(1LA)—C(2LC)—C(2LD) | 69(7) | C(5LD)—C(2L)—C(2LC)—C(2LB) | −176(7) |
| C(2L)—C(1LA)—C(2LC)—C(2LD) | 122(8) | C(1LC)—C(2L)—C(2LC)—C(2LB) | −32(4) |
| C(1LA)—C(2L)—C(2LC)—C(2LB) | −71(4) | C(2LD)—C(2LB)—C(2LC)—C(3LD) | −164(6) |
| C(2LD)—C(2L)—C(2LC)—C(2LB) | 70(5) | C(5LD)—C(2LB)—C(2LC)—C(3LD) | −49(3) |
| N(1L)—C(2L)—C(2LC)—C(2LB) | −36.6(17) | N(1L)—C(2LB)—C(2LC)—N(3L) | −24.1(16) |
| C(3LD)—C(2L)—C(2LC)—C(2LB) | −137(3) | C(1LC)—C(2LB)—C(2LC)—N(3L) | −85(2) |
| C(5LD)—C(2L)—C(2LC)—C(3LD) | −38(6) | C(2L)—C(2LB)—C(2LC)—N(3L) | −113(4) |
| C(1LC)—C(2L)—C(2LC)—C(3LD) | 105(5) | N(2L)—C(2LB)—C(2LC)—N(3L) | −44(5) |
| C(2LB)—C(2L)—C(2LC)—C(3LD) | 137(3) | C(1LA)—C(2LB)—C(2LC)—N(3L) | −3(3) |
| C(1LA)—C(2L)—C(2LC)—C(3LD) | 66(4) | C(2LD)—C(2LB)—C(2LC)—N(3L) | 134(4) |

TABLE 3-continued

Torsion angles [°] (cf. FIG. 4)

| | | | | |
|---|---|---|---|---|
| C(2LD)—C(2L)—C(2LC)—C(3LD) | −153(5) | C(5LD)—C(2LB)—C(2LC)—N(3L) | −110(3) |
| N(1L)—C(2L)—C(2LC)—C(3LD) | 100(3) | N(2L)—N(1L)—N(3L)—C(1LA) | −115(7) |
| C(5LD)—C(2L)—C(2LC)—N(3L) | −131(6) | C(2LB)—N(1L)—N(3L)—C(1LA) | −48(3) |
| C(1LC)—C(2L)—C(2LC)—N(3L) | 12(5) | C(1LC)—N(1L)—N(3L)—C(1LA) | 6(5) |
| C(2LB)—C(2L)—C(2LC)—N(3L) | 45(2) | O(10W)—N(1L)—N(3L)—C(1LA) | 80(3) |
| C(1LA)—C(2L)—C(2LC)—N(3L) | −26(3) | C(2L)—N(1L)—N(3L)—C(1LA) | −3(3) |
| C(2LD)—C(2L)—C(2LC)—N(3L) | 114(4) | N(2L)—N(1L)—N(3L)—C(2LB) | −67(7) |
| N(1L)—C(2L)—C(2LC)—N(3L) | 7.9(16) | C(1LC)—N(1L)—N(3L)—C(2LB) | 54(3) |
| C(3LD)—C(2L)—C(2LC)—N(3L) | −93(2) | C(1LA)—N(1L)—N(3L)—C(2LB) | 48(3) |
| N(1L)—C(2LB)—C(2LC)—C(1LA) | −21(3) | O(10W)—N(1L)—N(3L)—C(2LB) | 128(2) |
| C(1LC)—C(2LB)—C(2LC)—C(1LA) | −82(3) | C(2L)—N(1L)—N(3L)—C(2LB) | 45(2) |
| C(2L)—C(2LB)—C(2LC)—C(1LA) | −110(4) | C(2LB)—N(1L)—N(3L)—N(2L) | 67(7) |
| N(2L)—C(2LB)—C(2LC)—C(1LA) | −41(6) | C(1LC)—N(1L)—N(3L)—N(2L) | 121(9) |
| N(3L)—C(2LB)—C(2LC)—C(1LA) | 3(3) | C(1LA)—N(1L)—N(3L)—N(2L) | 115(7) |
| C(2LD)—C(2LB)—C(2LC)—C(1LA) | 137(5) | O(10W)—N(1L)—N(3L)—N(2L) | −166(8) |
| C(5LD)—C(2LB)—C(2LC)—C(1LA) | −107(5) | C(2L)—N(1L)—N(3L)—N(2L) | 112(8) |
| N(1L)—C(2LB)—C(2LC)—C(2LD) | −158(4) | N(2L)—N(1L)—N(3L)—C(2LC) | −100(7) |
| C(1LC)—C(2LB)—C(2LC)—C(2LD) | 140(4) | C(2LB)—N(1L)—N(3L)—C(2LC) | −33(2) |
| C(2L)—C(2LB)—C(2LC)—C(2LD) | 113(4) | C(1LC)—N(1L)—N(3L)—C(2LC) | 21(4) |
| N(2L)—C(2LB)—C(2LC)—C(2LD) | −178(6) | C(1LA)—N(1L)—N(3L)—C(2LC) | 14.8(19) |
| N(3L)—C(2LB)—C(2LC)—C(2LD) | −134(4) | O(10W)—N(1L)—N(3L)—C(2LC) | 94.3(19) |
| C(1LA)—C(2LB)—C(2LC)—C(2LD) | −137(5) | C(2L)—N(1L)—N(3L)—C(2LC) | 12(2) |
| C(5LD)—C(2LB)—C(2LC)—C(2LD) | 116(5) | N(2L)—N(1L)—N(3L)—C(1LC) | −121(9) |
| N(1L)—C(2LB)—C(2LC)—C(5LD) | 86(4) | C(2LB)—N(1L)—N(3L)—C(1LC) | −54(3) |
| C(1LC)—C(2LB)—C(2LC)—C(5LD) | 25(4) | C(1LA)—N(1L)—N(3L)—C(1LC) | −6(5) |
| C(2L)—C(2LB)—C(2LC)—C(5LD) | −3(4) | O(10W)—N(1L)—N(3L)—C(1LC) | 73(3) |
| N(2L)—C(2LB)—C(2LC)—C(5LD) | 66(6) | C(2L)—N(1L)—N(3L)—C(1LC) | −9(2) |
| N(3L)—C(2LB)—C(2LC)—C(5LD) | 110(3) | C(2LC)—C(1LA)—N(3L)—N(1L) | 43(5) |
| C(1LA)—C(2LB)—C(2LC)—C(5LD) | 107(5) | C(5LD)—C(1LA)—N(3L)—N(1L) | −5(4) |
| C(2LD)—C(2LB)—C(2LC)—C(5LD) | −116(5) | C(3LD)—C(1LA)—N(3L)—N(1L) | −68(4) |
| N(1L)—C(2LB)—C(2LC)—C(2L) | 89(4) | C(2LB)—C(1LA)—N(3L)—N(1L) | 38(2) |
| C(1LC)—C(2LB)—C(2LC)—C(2L) | 27(4) | C(2LD)—C(1LA)—N(3L)—N(1L) | 67(3) |
| N(2L)—C(2LB)—C(2LC)—C(2L) | 69(6) | C(2L)—C(1LA)—N(3L)—N(1L) | 3(3) |
| N(3L)—C(2LB)—C(2LC)—C(2L) | 113(4) | C(2LC)—C(1LA)—N(3L)—C(2LB) | 5(4) |
| C(1LA)—C(2LB)—C(2LC)—C(2L) | 110(4) | C(5LD)—C(1LA)—N(3L)—C(2LB) | −44(3) |
| C(2LD)—C(2LB)—C(2LC)—C(2L) | −113(5) | C(3LD)—C(1LA)—N(3L)—C(2LB) | −106(3) |
| C(5LD)—C(2LB)—C(2LC)—C(2L) | 3(4) | C(2LD)—C(1LA)—N(3L)—C(2LB) | 29(2) |
| N(1L)—C(2LB)—C(2LC)—C(3LD) | 37(4) | C(2L)—C(1LA)—N(3L)—C(2LB) | −35(2) |
| C(1LC)—C(2LB)—C(2LC)—C(3LD) | −24(4) | N(1L)—C(1LA)—N(3L)—C(2LB) | −38(2) |
| C(2L)—C(2LB)—C(2LC)—C(3LD) | −51(4) | C(2LC)—C(1LA)—N(3L)—N(2L) | 26(5) |
| N(2L)—C(2LB)—C(2LC)—C(3LD) | 17(7) | C(5LD)—C(1LA)—N(3L)—N(2L) | −22(4) |
| N(3L)—C(2LB)—C(2LC)—C(3LD) | 62(3) | C(3LD)—C(1LA)—N(3L)—N(2L) | −85(4) |
| C(1LA)—C(2LB)—C(2LC)—C(3LD) | 58(3) | C(2LB)—C(1LA)—N(3L)—N(2L) | 21(2) |
| C(2LD)—C(1LA)—N(3L)—N(2L) | 50(3) | C(1LC)—N(1L)—N(3L)—N(2L) | −41(7) |
| C(2L)—C(1LA)—N(3L)—N(2L) | −13(3) | C(2LB)—N(2L)—N(3L)—N(1L) | −101(8) |
| N(1L)—C(1LA)—N(3L)—N(2L) | −17(2) | C(4LD)—N(2L)—N(3L)—N(1L) | −44(9) |
| C(5LD)—C(1LA)—N(3L)—C(2LC) | −48(4) | N(1L)—N(2L)—N(3L)—C(1LA) | 73(8) |
| C(3LD)—C(1LA)—N(3L)—C(2LC) | −111(5) | C(1LC)—N(2L)—N(3L)—C(1LA) | 32(5) |
| C(2LB)—C(1LA)—N(3L)—C(2LC) | −5(4) | C(2LB)—N(2L)—N(3L)—C(1LA) | −28(3) |
| C(2LD)—C(1LA)—N(3L)—C(2LC) | 24(4) | C(4LD)—N(2L)—N(3L)—C(1LA) | 29(9) |
| C(2L)—C(1LA)—N(3L)—C(2LC) | −39(4) | N(1L)—N(2L)—N(3L)—C(2LB) | 101(8) |
| N(1L)—C(1LA)—N(3L)—C(2LC) | −43(5) | C(1LC)—N(2L)—N(3L)—C(2LB) | 60(2) |
| C(2LC)—C(1LA)—N(3L)—C(1LC) | 46(4) | C(4LD)—N(2L)—N(3L)—C(2LB) | 57(7) |
| C(5LD)—C(1LA)—N(3L)—C(1LC) | −3(3) | N(1L)—N(2L)—N(3L)—C(2LC) | 83(7) |
| C(3LD)—C(1LA)—N(3L)—C(1LC) | −65(3) | C(1LC)—N(2L)—N(3L)—C(2LC) | 41(3) |
| C(2LB)—C(1LA)—N(3L)—C(1LC) | 41.0(14) | C(2LB)—N(2L)—N(3L)—C(2LC) | −19(2) |
| C(2LD)—C(1LA)—N(3L)—C(1LC) | 70(2) | C(4LD)—N(2L)—N(3L)—C(2LC) | 38(8) |
| C(2L)—C(1LA)—N(3L)—C(1LC) | 6(2) | N(1L)—N(2L)—N(3L)—C(1LC) | 41(7) |
| N(1L)—C(1LA)—N(3L)—C(1LC) | 3(2) | C(2LB)—N(2L)—N(3L)—C(1LC) | −60(2) |
| C(1LC)—C(2LB)—N(3L)—N(1L) | −36(3) | C(4LD)—N(2L)—N(3L)—C(1LC) | −3(7) |
| C(2L)—C(2LB)—N(3L)—N(1L) | −91(4) | C(1LA)—C(2LC)—N(3L)—N(1L) | −142(5) |
| N(2L)—C(2LB)—N(3L)—N(1L) | 19(2) | C(2LD)—C(2LC)—N(3L)—N(1L) | 84(5) |
| C(2LC)—C(2LB)—N(3L)—N(1L) | −138(3) | C(5LD)—C(2LC)—N(3L)—N(1L) | −46(4) |
| C(1LA)—C(2LB)—N(3L)—N(1L) | −136(3) | C(2L)—C(2LC)—N(3L)—N(1L) | −18(4) |
| C(2LD)—C(2LB)—N(3L)—N(1L) | −162(3) | C(2LB)—C(2LC)—N(3L)—N(1L) | 33(2) |
| C(5LD)—C(2LB)—N(3L)—N(1L) | −107(3) | C(3LD)—C(2LC)—N(3L)—N(1L) | −98(3) |
| N(1L)—C(2LB)—N(3L)—C(1LA) | 136(3) | C(2LD)—C(2LC)—N(3L)—C(1LA) | −134(7) |
| C(1LC)—C(2LB)—N(3L)—C(1LA) | 100(2) | C(5LD)—C(2LC)—N(3L)—C(1LA) | 96(6) |
| C(2L)—C(2LB)—N(3L)—C(1LA) | 45(3) | C(2L)—C(2LC)—N(3L)—C(1LA) | 124(6) |
| N(2L)—C(2LB)—N(3L)—C(1LA) | 155(2) | C(2LB)—C(2LC)—N(3L)—C(1LA) | 174(5) |
| C(2LC)—C(2LB)—N(3L)—C(1LA) | −2.2(19) | C(3LD)—C(2LC)—N(3L)—C(1LA) | 43(4) |
| C(2LD)—C(2LB)—N(3L)—C(1LA) | −26(2) | C(1LA)—C(2LC)—N(3L)—C(2LB) | −174(5) |
| C(5LD)—C(2LB)—N(3L)—C(1LA) | 28.8(19) | C(2LD)—C(2LC)—N(3L)—C(2LB) | 52(4) |
| N(1L)—C(2LB)—N(3L)—N(2L) | −19(2) | C(5LD)—C(2LC)—N(3L)—C(2LB) | −79(4) |
| C(1LC)—C(2LB)—N(3L)—N(2L) | −56(2) | C(2L)—C(2LC)—N(3L)—C(2LB) | −51(3) |
| C(2L)—C(2LB)—N(3L)—N(2L) | −110(4) | C(3LD)—C(2LC)—N(3L)—C(2LB) | −131(3) |
| C(2LC)—C(2LB)—N(3L)—N(2L) | −158(3) | C(1LA)—C(2LC)—N(3L)—N(2L) | −157(4) |
| C(1LA)—C(2LB)—N(3L)—N(2L) | −155(2) | C(2LD)—C(2LC)—N(3L)—N(2L) | 69(5) |

TABLE 3-continued

Torsion angles [°] (cf. FIG. 4)

| | | | | |
|---|---|---|---|---|
| C(2LD)—C(2LB)—N(3L)—N(2L) | 179(3) | C(5LD)—C(2LC)—N(3L)—N(2L) | −62(4) |
| C(5LD)—C(2LB)—N(3L)—N(2L) | −126(3) | C(2L)—C(2LC)—N(3L)—N(2L) | −34(3) |
| N(1L)—C(2LB)—N(3L)—C(2LC) | 138(3) | C(2LB)—C(2LC)—N(3L)—N(2L) | 17(2) |
| C(1LC)—C(2LB)—N(3L)—C(2LC) | 102(3) | C(3LD)—C(2LC)—N(3L)—N(2L) | −114(2) |
| C(2L)—C(2LB)—N(3L)—C(2LC) | 47(3) | C(1LA)—C(2LC)—N(3L)—C(1LC) | −131(4) |
| N(2L)—C(2LB)—N(3L)—C(2LC) | 158(3) | C(2LB)—C(2LC)—N(3L)—C(1LC) | 95(5) |
| C(1LA)—C(2LB)—N(3L)—C(2LC) | 2.2(19) | C(5LD)—C(2LC)—N(3L)—C(1LC) | −35(4) |
| C(2LD)—C(2LB)—N(3L)—C(2LC) | −24(2) | C(2L)—C(2LC)—N(3L)—C(1LC) | −7(3) |
| C(5LD)—C(2LB)—N(3L)—C(2LC) | 31.0(16) | C(2LB)—C(2LC)—N(3L)—C(1LC) | 43.3(17) |
| N(1L)—C(2LB)—N(3L)—C(1LC) | 36(3) | C(3LD)—C(2LC)—N(3L)—C(1LC) | −88(2) |
| C(2L)—C(2LB)—N(3L)—C(1LC) | −55(3) | C(2L)—C(1LC)—N(3L)—N(1L) | 166(5) |
| N(2L)—C(2LB)—N(3L)—C(1LC) | 56(2) | N(2L)—C(1LC)—N(3L)—N(1L) | 21(4) |
| C(2LC)—C(2LB)—N(3L)—C(1LC) | −102(3) | C(2LB)—C(1LC)—N(3L)—N(1L) | 101(4) |
| C(1LA)—C(2LB)—N(3L)—C(1LC) | −100(2) | O(10W)—C(1LC)—N(3L)—N(1L) | −87(4) |
| C(2LD)—C(2LB)—N(3L)—C(1LC) | −125(3) | C(5LD)—C(1LC)—N(3L)—N(1L) | 176(4) |
| C(5LD)—C(2LB)—N(3L)—C(1LC) | −71(2) | N(1L)—C(1LC)—N(3L)—C(1LA) | −175(4) |
| C(2L)—C(1LC)—N(3L)—C(1LA) | −9(3) | N(3L)—C(2LC)—C(2LD)—C(2LB) | −37(3) |
| N(2L)—C(1LC)—N(3L)—C(1LA) | −153(3) | C(1LA)—C(2LC)—C(2LD)—C(2L) | −120(8) |
| C(2LB)—C(1LC)—N(3L)—C(1LA) | −74(2) | C(5LD)—C(2LC)—C(2LD)—C(2L) | 37(4) |
| O(10W)—C(1LC)—N(3L)—C(1LA) | 98(2) | C(2LB)—C(2LC)—C(2LD)—C(2L) | −52(4) |
| C(5LD)—C(1LC)—N(3L)—C(1LA) | 1.8(19) | C(3LD)—C(2LC)—C(2LD)—C(2L) | 96(11) |
| N(1L)—C(1LC)—N(3L)—C(2LB) | −101(4) | N(3L)—C(2LC)—C(2LD)—C(2L) | −89(4) |
| C(2L)—C(1LC)—N(3L)—C(2LB) | 65(3) | N(3L)—C(1LA)—C(2LD)—C(2LC) | −128(7) |
| N(2L)—C(1LC)—N(3L)—C(2LB) | −79(3) | C(5LD)—C(1LA)—C(2LD)—C(2LC) | −15(7) |
| O(10W)—C(1LC)—N(3L)—C(2LB) | 172(3) | C(3LD)—C(1LA)—C(2LD)—C(2LC) | 17(7) |
| C(5LD)—C(1LC)—N(3L)—C(2LB) | 76(3) | C(2LB)—C(1LA)—C(2LD)—C(2LC) | −100(7) |
| N(1L)—C(1LC)—N(3L)—N(2L) | −21(4) | C(2L)—C(1LA)—C(2LD)—C(2LC) | −46(7) |
| C(2L)—C(1LC)—N(3L)—N(2L) | 144(4) | N(1L)—C(1LA)—C(2LD)—C(2LC) | −103(7) |
| C(2LB)—C(1LC)—N(3L)—N(2L) | 79(3) | C(2LC)—C(1LA)—C(2LD)—C(5LD) | 15(7) |
| O(10W)—C(1LC)—N(3L)—N(2L) | −109(3) | N(3L)—C(1LA)—C(2LD)—C(5LD) | −113(3) |
| C(5LD)—C(1LC)—N(3L)—N(2L) | 155(3) | C(3LD)—C(1LA)—C(2LD)—C(5LD) | 32(3) |
| N(1L)—C(1LC)—N(3L)—C(2LC) | −158(4) | C(2LB)—C(1LA)—C(2LD)—C(5LD) | −85(3) |
| C(2L)—C(1LC)—N(3L)—C(2LC) | 8(3) | C(2L)—C(1LA)—C(2LD)—C(5LD) | −30(2) |
| N(2L)—C(1LC)—N(3L)—C(2LC) | −137(3) | N(1L)—C(1LA)—C(2LD)—C(5LD) | −88(3) |
| C(2LB)—C(1LC)—N(3L)—C(2LC) | −57(2) | C(2LC)—C(1LA)—C(2LD)—C(2LB) | 100(7) |
| O(10W)—C(1LC)—N(3L)—C(2LC) | 115(2) | N(3L)—C(1LA)—C(2LD)—C(2LB) | −27(2) |
| C(5LD)—C(1LC)—N(3L)—C(2LC) | 18.2(18) | C(5LD)—C(1LA)—C(2LD)—C(2LB) | 85(3) |
| O(3W)—O(1W)—O(2W)—O(6W) | 166(2) | C(3LD)—C(1LA)—C(2LD)—C(2LB) | 118(3) |
| O(6W)—O(1W)—O(2W)—O(3W) | −166(2) | C(2L)—C(1LA)—C(2LD)—C(2LB) | 55(3) |
| O(6W)—O(2W)—O(3W)—O(1W) | −10.2(17) | N(1L)—C(1LA)—C(2LD)—C(2LB) | −2.9(17) |
| O(6W)—O(1W)—O(3W)—O(2W) | 16(3) | C(2LC)—C(1LA)—C(2LD)—C(2L) | 46(7) |
| O(3W)—O(1W)—O(6W)—O(2W) | −16(3) | N(3L)—C(1LA)—C(2LD)—C(2L) | −82(3) |
| O(3W)—O(2W)—O(6W)—O(1W) | 15(2) | C(5LD)—C(1LA)—C(2LD)—C(2L) | 30(2) |
| N(3L)—N(1L)—O(10W)—C(1LC) | −130(3) | C(3LD)—C(1LA)—C(2LD)—C(2L) | 63(3) |
| N(2L)—N(1L)—O(10W)—C(1LC) | 57(3) | C(2LB)—C(1LA)—C(2LD)—C(2L) | −55(3) |
| C(2LB)—N(1L)—O(10W)—C(1LC) | −35(3) | N(1L)—C(1LA)—C(2LD)—C(2L) | −58(3) |
| C(1LA)—N(1L)—O(10W)—C(1LC) | −93(2) | N(1L)—C(2LB)—C(2LD)—C(2LC) | 30(5) |
| C(2L)—N(1L)—O(10W)—C(1LC) | −39(2) | C(1LC)—C(2LB)—C(2LD)—C(2LC) | −50(5) |
| C(2L)—C(1LC)—O(10W)—N(1L) | 100(4) | C(2L)—C(2LB)—C(2LD)—C(2LC) | −51(4) |
| N(2L)—C(1LC)—O(10W)—N(1L) | −40(2) | N(2L)—C(2LB)—C(2LD)—C(2LC) | 119(100) |
| C(2LB)—C(1LC)—O(10W)—N(1L) | 29(2) | N(3L)—C(2LB)—C(2LD)—C(2LC) | 45(4) |
| N(3L)—C(1LC)—O(10W)—N(1L) | 21.9(14) | C(1LA)—C(2LB)—C(2LD)—C(2LC) | 24(3) |
| C(5LD)—C(1LC)—O(10W)—N(1L) | 98(2) | C(5LD)—C(2LB)—C(2LD)—C(2LC) | −37(3) |
| C(5LD)—C(2LC)—C(2LD)—C(1LA) | 157(10) | N(1L)—C(2LB)—C(2LD)—C(1LA) | 6(4) |
| C(2L)—C(2LC)—C(2LD)—C(1LA) | 120(8) | C(1LC)—C(2LB)—C(2LD)—C(1LA) | −74(3) |
| C(2LB)—C(2LC)—C(2LD)—C(1LA) | 68(6) | C(2L)—C(2LB)—C(2LD)—C(1LA) | −74(3) |
| C(3LD)—C(2LC)—C(2LD)—C(1LA) | −143(15) | N(2L)—C(2LB)—C(2LD)—C(1LA) | 95(100) |
| N(3L)—C(2LC)—C(2LD)—C(1LA) | 31(4) | N(3L)—C(2LB)—C(2LD)—C(1LA) | 21.0(18) |
| C(1LA)—C(2LC)—C(2LD)—C(5LD) | −157(10) | C(2LC)—C(2LB)—C(2LD)—C(1LA) | −24(3) |
| C(2L)—C(2LC)—C(2LD)—C(5LD) | −37(4) | C(5LD)—C(2LB)—C(2LD)—C(1LA) | −61(2) |
| C(2LB)—C(2LC)—C(2LD)—C(5LD) | −89(5) | N(1L)—C(2LB)—C(2LD)—C(5LD) | 67(4) |
| C(3LD)—C(2LC)—C(2LD)—C(5LD) | 59(10) | C(1LC)—C(2LB)—C(2LD)—C(5LD) | −13(4) |
| N(3L)—C(2LC)—C(2LD)—C(5LD) | −126(6) | C(2L)—C(2LB)—C(2LD)—C(5LD) | −14(3) |
| C(1LA)—C(2LC)—C(2LD)—C(2LB) | −68(6) | N(2L)—C(2LB)—C(2LD)—C(5LD) | 156(100) |
| C(5LD)—C(2LC)—C(2LD)—C(2LB) | 89(5) | N(3L)—C(2LB)—C(2LD)—C(5LD) | 82(2) |
| C(2L)—C(2LC)—C(2LD)—C(2LB) | 52(4) | C(2LC)—C(2LB)—C(2LD)—C(5LD) | 37(3) |
| C(3LD)—C(2LC)—C(2LD)—C(2LB) | 149(11) | C(1LA)—C(2LB)—C(2LD)—C(5LD) | 61(2) |
| N(1L)—C(2LB)—C(2LD)—C(2L) | 81(4) | N(3L)—C(1LA)—C(3LD)—C(2L) | 81(4) |
| C(1LC)—C(2LB)—C(2LD)—C(2L) | 1(4) | C(5LD)—C(1LA)—C(3LD)—C(2L) | −19(3) |
| N(2L)—C(2LB)—C(2LD)—C(2L) | 169(100) | C(2LB)—C(1LA)—C(3LD)—C(2L) | 9(3) |
| N(3L)—C(2LB)—C(2LD)—C(2L) | 95(3) | C(2LD)—C(1LA)—C(3LD)—C(2L) | −57(3) |
| C(2LC)—C(2LB)—C(2LD)—C(2L) | 51(4) | N(1L)—C(1LA)—C(3LD)—C(2L) | 54(3) |
| C(1LA)—C(2LB)—C(2LD)—C(2L) | 74(3) | C(1LA)—C(3LD)—C(2L) | 133(5) |
| C(5LD)—C(2LB)—C(2LD)—C(2L) | 14(3) | C(2LD)—C(2LC)—C(3LD)—C(5LD) | −75(11) |
| C(5LD)—C(2L)—C(2LD)—C(2LC) | −52(6) | C(2L)—C(2LC)—C(3LD)—C(5LD) | 27(4) |
| C(1LC)—C(2L)—C(2LD)—C(2LC) | 97(7) | C(2LB)—C(2LC)—C(3LD)—C(5LD) | 69(4) |
| C(2LB)—C(2L)—C(2LD)—C(2LC) | 97(5) | N(3L)—C(2LC)—C(3LD)—C(5LD) | 110(4) |
| C(1LA)—C(2L)—C(2LD)—C(2LC) | 22(4) | C(2LD)—C(2LC)—C(3LD)—C(1LA) | 152(12) |

TABLE 3-continued

Torsion angles [°] (cf. FIG. 4)

| Atoms | Angle | Atoms | Angle |
|---|---|---|---|
| N(1L)—C(2L)—C(2LD)—C(2LC) | 72(5) | C(5LD)—C(2LC)—C(3LD)—C(1LA) | −133(5) |
| C(3LD)—C(2L)—C(2LD)—C(2LC) | −23(4) | C(2L)—C(2LC)—C(3LD)—C(1LA) | −106(4) |
| C(5LD)—C(2L)—C(2LD)—C(1LA) | −74(6) | C(2LB)—C(2LC)—C(3LD)—C(1LA) | −64(3) |
| C(1LC)—C(2L)—C(2LD)—C(1LA) | 75(5) | N(3L)—C(2LC)—C(3LD)—C(1LA) | −23(2) |
| C(2LC)—C(2L)—C(2LD)—C(1LA) | −22(4) | C(1LA)—C(2LC)—C(3LD)—O(9W)#1 | −122(5) |
| C(2LB)—C(2L)—C(2LD)—C(1LA) | 75(3) | C(2LD)—C(2LC)—C(3LD)—O(9W)#1 | 31(13) |
| N(1L)—C(2L)—C(2LD)—C(1LA) | 50(2) | C(5LD)—C(2LC)—C(3LD)—O(9W)#1 | 105(6) |
| C(3LD)—C(2L)—C(2LD)—C(1LA) | −45(2) | C(2L)—C(2LC)—C(3LD)—O(9W)#1 | 133(6) |
| C(1LC)—C(2L)—C(2LD)—C(5LD) | 149(9) | C(2LB)—C(2LC)—C(3LD)—O(9W)#1 | 174(4) |
| C(2LC)—C(2L)—C(2LD)—C(5LD) | 52(6) | N(3L)—C(2LC)—C(3LD)—O(9W)#1 | −144(5) |
| C(2LB)—C(2L)—C(2LD)—C(5LD) | 149(7) | C(1LA)—C(2LC)—C(3LD)—C(2L) | 106(4) |
| C(1LA)—C(2L)—C(2LD)—C(5LD) | 74(6) | C(2LD)—C(2LC)—C(3LD)—C(2L) | −102(12) |
| N(1L)—C(2L)—C(2LD)—C(5LD) | 124(7) | C(5LD)—C(2LC)—C(3LD)—C(2L) | −27(4) |
| C(3LD)—C(2L)—C(2LD)—C(5LD) | 29(5) | C(2LB)—C(2LC)—C(3LD)—C(2L) | 41(3) |
| C(5LD)—C(2L)—C(2LD)—C(2LB) | −149(7) | N(3L)—C(2LC)—C(3LD)—C(2L) | 83(3) |
| C(1LC)—C(2L)—C(2LD)—C(2LB) | 0(4) | C(1LC)—C(2L)—C(3LD)—C(5LD) | 177(12) |
| C(2LC)—C(2L)—C(2LD)—C(2LB) | −97(5) | C(2LC)—C(2L)—C(3LD)—C(5LD) | −73(9) |
| C(1LA)—C(2L)—C(2LD)—C(2LB) | −75(3) | C(2LB)—C(2L)—C(3LD)—C(5LD) | −119(11) |
| N(1L)—C(2L)—C(2LD)—C(2LB) | −25.5(19) | C(1LA)—C(2L)—C(3LD)—C(5LD) | −109(9) |
| C(3LD)—C(2L)—C(2LD)—C(2LB) | −120(4) | C(2LD)—C(2L)—C(3LD)—C(5LD) | −59(9) |
| C(2LC)—C(1LA)—C(3LD)—C(5LD) | −31(3) | N(1L)—C(2L)—C(3LD)—C(5LD) | −151(10) |
| N(3L)—C(1LA)—C(3LD)—C(5LD) | 100(4) | C(5LD)—C(2L)—C(3LD)—C(1LA) | 109(9) |
| C(2LB)—C(1LA)—C(3LD)—C(5LD) | 28(4) | C(1LC)—C(2L)—C(3LD)—C(1LA) | −75(4) |
| C(2LD)—C(1LA)—C(3LD)—C(5LD) | −38(3) | C(2LC)—C(2L)—C(3LD)—C(1LA) | 36(2) |
| C(2L)—C(1LA)—C(3LD)—C(5LD) | 19(3) | C(2LB)—C(2L)—C(3LD)—C(1LA) | −10(4) |
| N(1L)—C(1LA)—C(3LD)—C(5LD) | 73(3) | C(2LD)—C(2L)—C(3LD)—C(1LA) | 49(3) |
| N(3L)—C(1LA)—C(3LD)—C(2LC) | 131(4) | N(1L)—C(2L)—C(3LD)—C(1LA) | −42(2) |
| C(5LD)—C(1LA)—C(3LD)—C(2LC) | 31(3) | C(5LD)—C(2L)—C(3LD)—C(2LC) | 73(9) |
| C(2LB)—C(1LA)—C(3LD)—C(2LC) | 58(3) | C(1LC)—C(2L)—C(3LD)—C(2LC) | −111(6) |
| C(2LD)—C(1LA)—C(3LD)—C(2LC) | −7(3) | C(2LB)—C(2L)—C(3LD)—C(2LC) | −46(4) |
| C(2L)—C(1LA)—C(3LD)—C(2LC) | 50(3) | C(1LA)—C(2L)—C(3LD)—C(2LC) | −36(2) |
| N(1L)—C(1LA)—C(3LD)—C(2LC) | 104(3) | C(2LD)—C(2L)—C(3LD)—C(2LC) | 14(3) |
| C(2LC)—C(1LA)—C(3LD)—O(9W)#1 | 97(6) | N(1L)—C(2L)—C(3LD)—C(2LC) | −78(3) |
| N(3L)—C(1LA)—C(3LD)—O(9W)#1 | −132(5) | C(5LD)—C(2L)—C(3LD)—O(9W)#1 | −34(12) |
| C(5LD)—C(1LA)—C(3LD)—O(9W)#1 | 128(7) | C(1LC)—C(2L)—C(3LD)—O(9W)#1 | 143(6) |
| C(2LB)—C(1LA)—C(3LD)—O(9W)#1 | 156(5) | C(2LC)—C(2L)—C(3LD)—O(9W)#1 | −107(7) |
| C(2LD)—C(1LA)—C(3LD)—O(9W)#1 | 90(6) | C(2LB)—C(2L)—C(3LD)—O(9W)#1 | −153(6) |
| C(2L)—C(1LA)—C(3LD)—O(9W)#1 | 147(7) | C(1LA)—C(2L)—C(3LD)—O(9W)#1 | −142(7) |
| N(1L)—C(1LA)—C(3LD)—O(9W)#1 | −159(5) | C(2LD)—C(2L)—C(3LD)—O(9W)#1 | −93(7) |
| C(2LC)—C(1LA)—C(3LD)—C(2L) | −50(3) | N(1L)—C(2L)—C(3LD)—O(9W)#1 | 175(6) |
| N(1L)—N(2L)—C(4LD)—O(11W)#3 | 126(7) | C(2L)—C(2LC)—C(5LD)—C(1LA) | −85(7) |
| C(1LC)—N(2L)—C(4LD)—O(11W)#3 | 140(6) | C(2LB)—C(2LC)—C(5LD)—C(1LA) | −81(4) |
| C(2LB)—N(2L)—C(4LD)—O(11W)#3 | −170(5) | C(3LD)—C(2LC)—C(5LD)—C(1LA) | 46(5) |
| N(3L)—N(2L)—C(4LD)—O(11W)#3 | 143(7) | N(3L)—C(2LC)—C(5LD)—C(1LA) | −33(2) |
| C(1LC)—C(2L)—C(5LD)—C(2LC) | −92(15) | C(1LA)—C(2LC)—C(5LD)—C(2LD) | 163(7) |
| C(2LB)—C(2L)—C(5LD)—C(2LC) | −5(9) | C(2L)—C(2LC)—C(5LD)—C(2LD) | 78(8) |
| C(1LA)—C(2L)—C(5LD)—C(2LC) | −32(2) | C(2LB)—C(2LC)—C(5LD)—C(2LD) | 82(5) |
| C(2LD)—C(2L)—C(5LD)—C(2LC) | 30(3) | C(3LD)—C(2LC)—C(5LD)—C(2LD) | −151(5) |
| N(1L)—C(2L)—C(5LD)—C(2LC) | −51(7) | N(3L)—C(2LC)—C(5LD)—C(2LD) | 130(6) |
| C(3LD)—C(2L)—C(5LD)—C(2LC) | −86(8) | C(1LA)—C(2LC)—C(5LD)—C(1LC) | 65(4) |
| C(1LC)—C(2L)—C(5LD)—C(3LD) | −6(21) | C(2LD)—C(2LC)—C(5LD)—C(1LC) | −98(5) |
| C(2LC)—C(2L)—C(5LD)—C(3LD) | 86(8) | C(2L)—C(2LC)—C(5LD)—C(1LC) | −19(5) |
| C(2LB)—C(2L)—C(5LD)—C(3LD) | 81(11) | C(2LB)—C(2LC)—C(5LD)—C(1LC) | −15(2) |
| C(1LA)—C(2L)—C(5LD)—C(3LD) | 54(7) | C(3LD)—C(2LC)—C(5LD)—C(1LC) | 111(3) |
| C(2LD)—C(2L)—C(5LD)—C(3LD) | 116(8) | N(3L)—C(2LC)—C(5LD)—C(1LC) | 32(3) |
| N(1L)—C(2L)—C(5LD)—C(3LD) | 35(11) | C(1LA)—C(2LC)—C(5LD)—C(2LB) | 81(4) |
| C(1LC)—C(2L)—C(5LD)—C(1LA) | −60(15) | C(2LD)—C(2LC)—C(5LD)—C(2LB) | −82(5) |
| C(2LC)—C(2L)—C(5LD)—C(1LA) | 32(2) | C(2L)—C(2LC)—C(5LD)—C(2LB) | −4(6) |
| C(2LB)—C(2L)—C(5LD)—C(1LA) | 27(8) | C(3LD)—C(2LC)—C(5LD)—C(2LB) | 127(3) |
| C(2LD)—C(2L)—C(5LD)—C(1LA) | 62(2) | N(3L)—C(2LC)—C(5LD)—C(2LB) | 47.9(18) |
| N(1L)—C(2L)—C(5LD)—C(1LA) | −19(6) | C(1LA)—C(3LD)—C(5LD)—C(2L) | −62(9) |
| C(3LD)—C(2L)—C(5LD)—C(1LA) | −54(7) | C(2LC)—C(3LD)—C(5LD)—C(2L) | −86(9) |
| C(1LC)—C(2L)—C(5LD)—C(2LD) | −121(14) | O(9W)#1—C(3LD)—C(5LD)—C(2L) | 157(8) |
| C(2LC)—C(2L)—C(5LD)—C(2LD) | −30(3) | C(1LA)—C(3LD)—C(5LD)—C(2LC) | 24(3) |
| C(2LB)—C(2L)—C(5LD)—C(2LD) | −35(8) | O(9W)#1—C(3LD)—C(5LD)—C(2LC) | −117(5) |
| C(1LA)—C(2L)—C(5LD)—C(2LD) | −62(2) | C(2L)—C(3LD)—C(5LD)—C(2LC) | 86(9) |
| N(1L)—C(2L)—C(5LD)—C(2LD) | −80(6) | C(2LC)—C(3LD)—C(5LD)—C(1LA) | −24(3) |
| C(3LD)—C(2L)—C(5LD)—C(2LD) | −116(8) | O(9W)#1—C(3LD)—C(5LD)—C(1LA) | −142(5) |
| C(2LC)—C(2L)—C(5LD)—C(1LC) | 92(15) | C(2L)—C(3LD)—C(5LD)—C(1LA) | 62(9) |
| C(2LB)—C(2L)—C(5LD)—C(1LC) | 86(16) | C(1LA)—C(3LD)—C(5LD)—C(2LD) | 40(3) |
| C(1LA)—C(2L)—C(5LD)—C(1LC) | 60(15) | C(2LC)—C(3LD)—C(5LD)—C(2LD) | 15(3) |
| C(2LD)—C(2L)—C(5LD)—C(1LC) | 121(14) | O(9W)#1—C(3LD)—C(5LD)—C(2LD) | −102(5) |
| N(1L)—C(2L)—C(5LD)—C(1LC) | 41(11) | C(2L)—C(3LD)—C(5LD)—C(2LD) | 101(10) |
| C(3LD)—C(2L)—C(5LD)—C(1LC) | 6(21) | C(1LA)—C(3LD)—C(5LD)—C(1LC) | −64(3) |
| C(1LC)—C(2L)—C(5LD)—C(2LB) | −86(16) | C(2LC)—C(3LD)—C(5LD)—C(1LC) | −88(4) |
| C(2LC)—C(2L)—C(5LD)—C(2LB) | 5(9) | O(9W)#1—C(3LD)—C(5LD)—C(1LC) | 155(4) |
| C(1LA)—C(2L)—C(5LD)—C(2LB) | −27(8) | C(2L)—C(3LD)—C(5LD)—C(1LC) | −2(7) |
| C(2LD)—C(2L)—C(5LD)—C(2LB) | 35(8) | C(1LA)—C(3LD)—C(5LD)—C(2LB) | −23(3) |

TABLE 3-continued

Torsion angles [°] (cf. FIG. 4)

| Atoms | Angle | Atoms | Angle |
|---|---|---|---|
| N(1L)—C(2L)—C(5LD)—C(2LB) | −45(5) | C(2LC)—C(3LD)—C(5LD)—C(2LB) | −47(3) |
| C(3LD)—C(2L)—C(5LD)—C(2LB) | −81(11) | O(9W)#1—C(3LD)—C(5LD)—C(2LB) | −164(4) |
| C(1LA)—C(2LC)—C(5LD)—C(2L) | 85(7) | C(2L)—C(3LD)—C(5LD)—C(2LB) | 39(8) |
| C(2LD)—C(2LC)—C(5LD)—C(2L) | −78(8) | C(2LC)—C(1LA)—C(5LD)—C(2L) | −94(7) |
| C(2LB)—C(2LC)—C(5LD)—C(2L) | 4(6) | N(3L)—C(1LA)—C(5LD)—C(2L) | 20(7) |
| C(3LD)—C(2LC)—C(5LD)—C(2L) | 130(7) | C(3LD)—C(1LA)—C(5LD)—C(2L) | 138(7) |
| N(3L)—C(2LC)—C(5LD)—C(2L) | 52(7) | C(2LB)—C(1LA)—C(5LD)—C(2L) | −18(6) |
| C(1LA)—C(2LC)—C(5LD)—C(3LD) | −46(5) | C(2LD)—C(1LA)—C(5LD)—C(2L) | −84(6) |
| C(2LD)—C(2LC)—C(5LD)—C(3LD) | 151(5) | N(1L)—C(1LA)—C(5LD)—C(2L) | 17(6) |
| C(2L)—C(2LC)—C(5LD)—C(3LD) | −130(7) | N(3L)—C(1LA)—C(5LD)—C(2LC) | 113(5) |
| C(2LB)—C(2LC)—C(5LD)—C(3LD) | −127(3) | C(3LD)—C(1LA)—C(5LD)—C(2LC) | −129(5) |
| N(3L)—C(2LC)—C(5LD)—C(3LD) | −79(4) | C(2LB)—C(1LA)—C(5LD)—C(2LC) | 76(4) |
| C(2LD)—C(2LC)—C(5LD)—C(1LA) | −163(7) | C(2LD)—C(1LA)—C(5LD)—C(2LC) | 10(4) |
| C(2L)—C(1LA)—C(5LD)—C(2LC) | 94(7) | N(3L)—C(1LC)—C(5LD)—C(2L) | −119(16) |
| N(1L)—C(1LA)—C(5LD)—C(2LC) | 111(4) | N(1L)—C(1LC)—C(5LD)—C(2LC) | −30(4) |
| C(2LC)—C(1LA)—C(5LD)—C(3LD) | 129(5) | C(2L)—C(1LC)—C(5LD)—C(2LC) | 88(16) |
| N(3L)—C(1LA)—C(5LD)—C(3LD) | −118(3) | N(2L)—C(1LC)—C(5LD)—C(2LC) | 4(6) |
| C(2LB)—C(1LA)—C(5LD)—C(3LD) | −156(3) | C(2LB)—C(1LC)—C(5LD)—C(2LC) | 21(3) |
| C(2LD)—C(1LA)—C(5LD)—C(3LD) | 138(4) | O(10W)—C(1LC)—C(5LD)—C(2LC) | −98(3) |
| C(2L)—C(1LA)—C(5LD)—C(3LD) | −138(7) | N(3L)—C(1LC)—C(5LD)—C(2LC) | −31(3) |
| N(1L)—C(1LA)—C(5LD)—C(3LD) | −120(3) | N(1L)—C(1LC)—C(5LD)—C(3LD) | 58(4) |
| C(2LC)—C(1LA)—C(5LD)—C(2LD) | −10(4) | C(2L)—C(1LC)—C(5LD)—C(3LD) | 175(17) |
| N(3L)—C(1LA)—C(5LD)—C(2LD) | 104(3) | N(2L)—C(1LC)—C(5LD)—C(3LD) | 92(6) |
| C(3LD)—C(1LA)—C(5LD)—C(2LD) | −138(4) | C(2LB)—C(1LC)—C(5LD)—C(3LD) | 108(4) |
| C(2LB)—C(1LA)—C(5LD)—C(2LD) | 66(2) | O(10W)—C(1LC)—C(5LD)—C(3LD) | −11(4) |
| C(2L)—C(1LA)—C(5LD)—C(2LD) | 84(6) | N(3L)—C(1LC)—C(5LD)—C(3LD) | 56(3) |
| N(1L)—C(1LA)—C(5LD)—C(2LD) | 101(2) | N(1L)—C(1LC)—C(5LD)—C(1LA) | 0(2) |
| C(2LC)—C(1LA)—C(5LD)—C(1LC) | −111(5) | C(2L)—C(1LC)—C(5LD)—C(1LA) | 117(16) |
| N(3L)—C(1LA)—C(5LD)—C(1LC) | 3(3) | N(2L)—C(1LC)—C(5LD)—C(1LA) | 34(5) |
| C(3LD)—C(1LA)—C(5LD)—C(1LC) | 121(3) | C(2LB)—C(1LC)—C(5LD)—C(1LA) | 50(2) |
| C(2LB)—C(1LA)—C(5LD)—C(1LC) | −35.0(16) | O(10W)—C(1LC)—C(5LD)—C(1LA) | −69(2) |
| C(2LD)—C(1LA)—C(5LD)—C(1LC) | −101(3) | N(3L)—C(1LC)—C(5LD)—C(1LA) | −1.5(16) |
| C(2L)—C(1LA)—C(5LD)—C(1LC) | −17(5) | N(1L)—C(1LC)—C(5LD)—C(2LD) | −60(3) |
| N(1L)—C(1LA)—C(5LD)—C(1LC) | 0.1(16) | C(2L)—C(1LC)—C(5LD)—C(2LD) | 58(15) |
| C(2LC)—C(1LA)—C(5LD)—C(2LB) | −76(4) | N(2L)—C(1LC)—C(5LD)—C(2LD) | −25(6) |
| N(3L)—C(1LA)—C(5LD)—C(2LB) | 38(2) | C(2LB)—C(1LC)—C(5LD)—C(2LD) | −9(3) |
| C(3LD)—C(1LA)—C(5LD)—C(2LB) | 156(3) | O(10W)—C(1LC)—C(5LD)—C(2LD) | −128(3) |
| C(2LD)—C(1LA)—C(5LD)—C(2LB) | −66(2) | N(3L)—C(1LC)—C(5LD)—C(2LD) | −61(2) |
| C(2L)—C(1LA)—C(5LD)—C(2LB) | 18(6) | N(1L)—C(1LC)—C(5LD)—C(2LB) | −50(2) |
| N(1L)—C(1LA)—C(5LD)—C(2LB) | 35.1(13) | C(2L)—C(1LC)—C(5LD)—C(2LB) | 67(15) |
| C(2LC)—C(2LD)—C(5LD)—C(2L) | 99(8) | N(2L)—C(1LC)—C(5LD)—C(2LB) | −16(4) |
| C(1LA)—C(2LD)—C(5LD)—C(2L) | 89(6) | O(10W)—C(1LC)—C(5LD)—C(2LB) | −119(3) |
| C(2LB)—C(2LD)—C(5LD)—C(2L) | 23(6) | N(3L)—C(1LC)—C(5LD)—C(2LB) | −51.7(18) |
| C(1LA)—C(2LD)—C(5LD)—C(2LC) | −10(4) | N(1L)—C(2LB)—C(5LD)—C(2L) | 86(10) |
| C(2LB)—C(2LD)—C(5LD)—C(2LC) | −76(5) | C(1LC)—C(2LB)—C(5LD)—C(2L) | 32(9) |
| C(2L)—C(2LD)—C(5LD)—C(2LC) | −99(8) | N(2L)—C(2LB)—C(5LD)—C(2L) | 44(10) |
| C(2LC)—C(2LD)—C(5LD)—C(3LD) | −32(6) | N(3L)—C(2LB)—C(5LD)—C(2L) | 121(10) |
| C(1LA)—C(2LD)—C(5LD)—C(3LD) | −42(4) | C(2LC)—C(2LB)—C(5LD)—C(2L) | −173(11) |
| C(2LB)—C(2LD)—C(5LD)—C(3LD) | −108(4) | C(1LA)—C(2LB)—C(5LD)—C(2L) | 147(10) |
| C(2L)—C(2LD)—C(5LD)—C(3LD) | −131(8) | C(2LD)—C(2LB)—C(5LD)—C(2L) | −136(10) |
| C(2LC)—C(2LD)—C(5LD)—C(1LA) | 10(4) | N(1L)—C(2LB)—C(5LD)—C(2LC) | −101(4) |
| C(2LB)—C(2LD)—C(5LD)—C(1LA) | −66(2) | C(1LC)—C(2LB)—C(5LD)—C(2LC) | −154(4) |
| C(2L)—C(2LD)—C(5LD)—C(1LA) | −89(6) | C(2L)—C(2LB)—C(5LD)—C(2LC) | 173(11) |
| C(2LC)—C(2LD)—C(5LD)—C(1LC) | 83(5) | N(2L)—C(2LB)—C(5LD)—C(2LC) | −142(4) |
| C(1LA)—C(2LD)—C(5LD)—C(1LC) | 73(2) | N(3L)—C(2LB)—C(5LD)—C(2LC) | −66(3) |
| C(2LB)—C(2LD)—C(5LD)—C(1LC) | 7(2) | C(1LA)—C(2LB)—C(5LD)—C(2LC) | −39(3) |
| C(2L)—C(2LD)—C(5LD)—C(1LC) | −16(5) | C(2LD)—C(2LB)—C(5LD)—C(2LC) | 37(3) |
| C(2LC)—C(2LD)—C(5LD)—C(2LB) | 76(5) | N(1L)—C(2LB)—C(5LD)—C(3LD) | −36(4) |
| C(1LA)—C(2LD)—C(5LD)—C(2LB) | 66(2) | C(1LC)—C(2LB)—C(5LD)—C(3LD) | −89(4) |
| C(2L)—C(2LD)—C(5LD)—C(2LB) | −23(6) | C(2L)—C(2LB)—C(5LD)—C(3LD) | −122(11) |
| N(1L)—C(1LC)—C(5LD)—C(2L) | −118(16) | N(2L)—C(2LB)—C(5LD)—C(3LD) | −78(5) |
| N(2L)—C(1LC)—C(5LD)—C(2L) | −83(16) | N(3L)—C(2LB)—C(5LD)—C(3LD) | −1(4) |
| C(2LB)—C(1LC)—C(5LD)—C(2L) | −67(15) | C(2LC)—C(2LB)—C(5LD)—C(3LD) | 65(4) |
| O(10W)—C(1LC)—C(5LD)—C(2L) | 174(16) | C(1LA)—C(2LB)—C(5LD)—C(3LD) | 25(3) |
| C(2LD)—C(2LB)—C(5LD)—C(3LD) | 102(5) | N(2L)—C(2LB)—C(5LD)—C(2LD) | −179(4) |
| N(1L)—C(2LB)—C(5LD)—C(1LA) | −62(2) | N(3L)—C(2LB)—C(5LD)—C(2LD) | −103(3) |
| C(1LC)—C(2LB)—C(5LD)—C(1LA) | −115(3) | C(2LC)—C(2LB)—C(5LD)—C(2LD) | −37(3) |
| C(2L)—C(2LB)—C(5LD)—C(1LA) | −147(10) | C(1LA)—C(2LB)—C(5LD)—C(2LD) | −76(2) |
| N(2L)—C(2LB)—C(5LD)—C(1LA) | −103(4) | N(1L)—C(2LB)—C(5LD)—C(1LC) | 53(2) |
| N(3L)—C(2LB)—C(5LD)—C(1LA) | −26.3(17) | C(2L)—C(2LB)—C(5LD)—C(1LC) | −32(9) |
| C(2LC)—C(2LB)—C(5LD)—C(1LA) | 39(3) | N(2L)—C(2LB)—C(5LD)—C(1LC) | 12(3) |
| C(2LD)—C(2LB)—C(5LD)—C(1LA) | 76(3) | N(3L)—C(2LB)—C(5LD)—C(1LC) | 88(2) |
| N(1L)—C(2LB)—C(5LD)—C(1LC) | −138(3) | C(2LC)—C(2LB)—C(5LD)—C(1LC) | 154(4) |
| C(1LC)—C(2LB)—C(5LD)—C(2LD) | 169(3) | C(1LA)—C(2LB)—C(5LD)—C(1LC) | 115(3) |
| C(2L)—C(2LB)—C(5LD)—C(2LD) | 136(10) | C(2LD)—C(2LB)—C(5LD)—C(1LC) | −169(3) |

Symmetry transformations used to generate equivalent atoms:
-1x+1,y,-z+1 #2-x+1,y-1,-z+1 #3-x+1,y+1,-z+1

The invention claimed is:
1. A process for the manufacture of a purified form of a compound of formula (I):

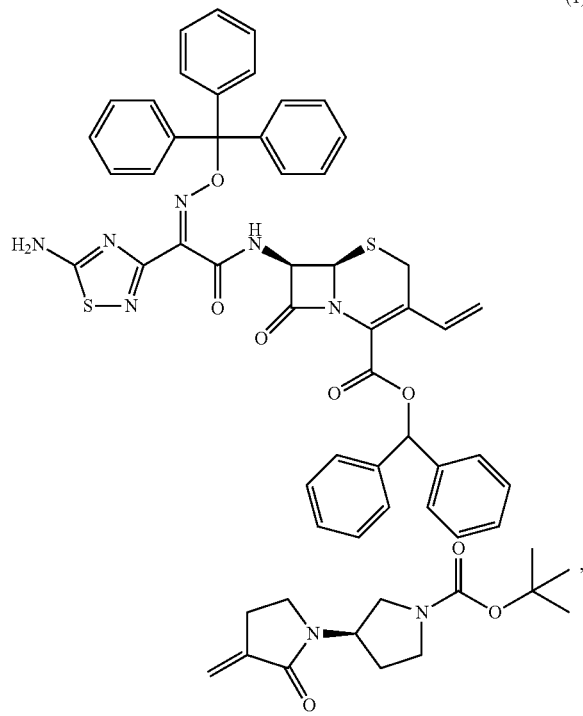

(I)

from a raw form of said compound, comprising the steps of:
converting said raw compound of formula (I) into a solid DMSO solvate;
isolating said DMSO solvate;
re-dissolving said isolated DMSO solvate in methylene chloride in which said compound of formula (I) precipitates; and
isolating said precipitated purified compound of formula (I).

2. The process according to claim 1, wherein the raw compound of formula (I) is converted into a solid DMSO solvate by suspending said raw compound of formula (I) in ethyl acetate, adding DMSO to said suspension in an amount sufficient to dissolve the compound of formula (I) and separating the DMSO solvate of the compound of formula (I), which precipitates from the solution, from the liquid phase.

3. The process according to claim 2, wherein the solid DMSO solvate is crystalline or substantially crystalline.

4. The process according to claim 2, wherein the molar ratio of the compound of formula (I) and DMSO in said solid DMSO solvate is from about 1:1.75 to about 1:2.75.

5. The process according to claim 4, wherein the molar ratio of the compound of formula (I) and DMSO is from about 1:2 to about 1:2.5.

6. The process according to claim 2, wherein the solid DMSO solvate is isolated in wet form.

7. The process according to claim 2, wherein the solution is cooled to about 0 to 4° C. during and/or after re-dissolving the DMSO solvate.

8. A process for the manufacture of a solid DMSO solvate of the compound of formula (I)

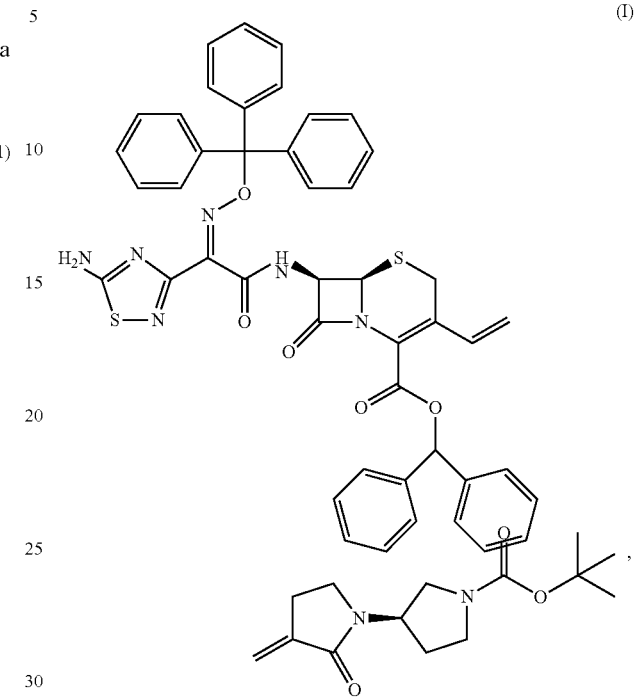

(I)

comprising the steps of:
suspending a raw compound of formula (I) in ethyl acetate;
adding DMSO to said suspension in an amount sufficient to dissolve the compound of formula (I) into a DMSO solvate;
separating said DMSO solvate of the compound of formula (I) from the liquid phase; and
processing said DMSO solvate without previously drying it.

9. A process for the manufacture of a solid DMSO solvate of the compound of formula (I):

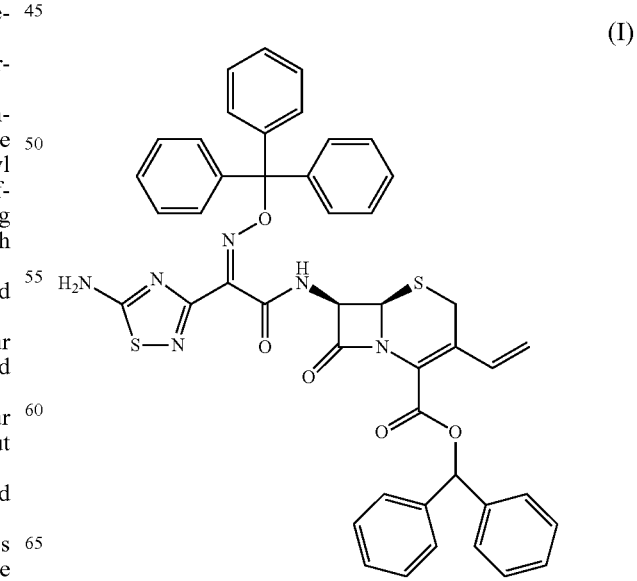

(I)

-continued

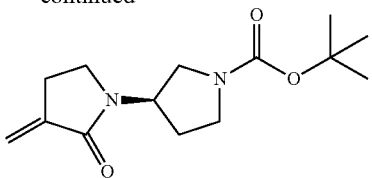

comprising the steps of:
  suspending raw compound of formula (I) in ethyl acetate;
  adding DMSO to said suspension in an amount sufficient to dissolve the compound of formula (I) to form a DMSO solvate; and
  separating said DMSO solvate from the liquid phase, wherein the raw compound of formula (I) is manufactured by reacting (1'-tert-butoxycarbonyl-2-oxo-[1,3']-(R)-bipyrrolidinyl-3-(R,S)-yl)-triphenyl-phosphonium bromide with 7-[2-(5-amino-[1,2,4]thiadiazol-3-yl)-2-trityloxyimino-acetylamino]-3-formyl-8-oxo-5-thia-1-aza-bicyclo[4.2.0]oct-2-ene-2-carboxylic acid benzhydryl ester in a mixture of methylene chloride/toluene/THF in presence of t-$C_4H_9$OK.

10. The process according to claim 9, wherein the raw compound of formula (I) is further processed without previously drying it, which process comprises the step of removing residual methylene chloride from the suspension of the raw compound of formula (I) in ethyl acetate before adding the DMSO to said suspension.

11. The process according to claim 10, wherein the residual methylene chloride is distilled off from the suspension.

* * * * *